US011857577B2

(12) United States Patent
McKenna

(10) Patent No.: US 11,857,577 B2
(45) Date of Patent: Jan. 2, 2024

(54) COMPOSITIONS AND METHODS FOR THE TREATMENT OF HEPATIC DISEASES AND DISORDERS

(71) Applicant: Labyrinth Holdings, LLC, Houston, TX (US)

(72) Inventor: Elizabeth McKenna, Houston, TX (US)

(73) Assignee: Labyrinth Holdings, LLC, Houston, TX (US)

( * ) Notice: Subject to any disclaimer, the term of this patent is extended or adjusted under 35 U.S.C. 154(b) by 0 days.

(21) Appl. No.: 16/172,825

(22) Filed: Oct. 28, 2018

(65) Prior Publication Data

US 2019/0290703 A1 Sep. 26, 2019

Related U.S. Application Data

(63) Continuation of application No. 15/626,055, filed on Jun. 16, 2017, now Pat. No. 10,149,869, which is a continuation of application No. 13/743,194, filed on Jan. 16, 2013, now Pat. No. 9,713,630.

(60) Provisional application No. 61/586,975, filed on Jan. 16, 2012.

(51) Int. Cl.
| | | |
|---|---|---|
| *A61K 35/74* | (2015.01) | |
| *A61K 38/48* | (2006.01) | |
| *A61K 35/742* | (2015.01) | |
| *A61K 35/744* | (2015.01) | |
| *A61K 9/00* | (2006.01) | |
| *A61K 9/68* | (2006.01) | |

(52) U.S. Cl.
CPC ............ *A61K 35/74* (2013.01); *A61K 35/742* (2013.01); *A61K 35/744* (2013.01); *A61K 38/482* (2013.01); *C12Y 304/21043* (2013.01); *A61K 9/0056* (2013.01); *A61K 9/0058* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 3,806,290 A | 4/1974 | Graff et al. | |
| 4,322,405 A | 3/1982 | Schulthess et al. | |
| 5,716,615 A | 2/1998 | Vesely et al. | |
| 5,955,321 A | 9/1999 | Bijl et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,281,191 B1 | 8/2001 | Slesarev et al. | |
| 6,339,068 B1 | 1/2002 | Krieg et al. | |
| 6,767,557 B2 | 7/2004 | Ulrich et al. | |
| 7,265,152 B2 | 9/2007 | Saha et al. | |
| 7,959,911 B2 | 6/2011 | Desimone | |
| 8,007,783 B2 | 8/2011 | Miller | |
| 8,278,089 B2 | 10/2012 | Miller | |
| 8,304,226 B2 | 11/2012 | Miller | |
| 9,713,630 B2 | 7/2017 | McKenna et al. | |
| 9,931,398 B2 | 4/2018 | McKenna et al. | |
| 2002/0164341 A1 | 11/2002 | Davis et al. | |
| 2004/0129174 A1 | 7/2004 | Li et al. | |
| 2005/0124053 A1 | 6/2005 | Moen et al. | |
| 2006/0286205 A1 | 12/2006 | Fichtali et al. | |
| 2007/0179101 A1 | 8/2007 | Kitagawa et al. | |
| 2008/0045473 A1 | 2/2008 | Uhlmann et al. | |
| 2008/0050353 A1* | 2/2008 | Miller .................... | A61K 9/006 424/93.45 |
| 2009/0297561 A1 | 12/2009 | Pasternack et al. | |
| 2010/0159072 A1* | 6/2010 | Endo ......................... | A23F 3/10 426/61 |
| 2011/0104134 A1 | 5/2011 | Ihara et al. | |

FOREIGN PATENT DOCUMENTS

| | | |
|---|---|---|
| EP | 1178118 | 2/2002 |
| EP | 1920774 | 5/2008 |
| FR | 2951377 | 4/2011 |
| JP | H04264034 | 9/1992 |
| JP | H0656680 | 3/1994 |
| JP | 09301878 | 11/1997 |

(Continued)

OTHER PUBLICATIONS

Zakostelska et al (PLOS One, vol. 6, Issue 11, e27961:1-11,2011). (Year: 2011).*
Bron et al (Nature Rev. Microbiol., 10:66-78, 2012).*
Basu et al., "Raised levels of F(2)-isoprostanes and prostaglandin F(2alpha) in different rheumatic diseases," Ann Rheum Dis. 60(6):1627-31 (2001).
Blanton et al., "Probiotics Blunt the Anti-Hypertensive Effect of Blueberry Feeding in Hypertensive Rats without Altering Hippuric Acid Production," PLoS One 10(11):(1-14) (2015).
Chassy et al., "Method for the lysis of Gram-positive, asporogenous bacteria with lysozyme," Appl Environ Microbiol. 39(1):153-8 (1980).
Halliwell et al., "Measuring reactive species and oxidative damage in vivo and in cell culture: how should you do it and what do the results mean?" Br J Pharmacol. 142(2):231-55 (2004).

(Continued)

*Primary Examiner* — Brian Gangle
(74) *Attorney, Agent, or Firm* — McDonnell Boehnen Hulbert & Berghoff LLP

(57) ABSTRACT

The disclosure provides oral compositions and methods of using such compositions in treating subjects infected with one or more hepatic disorders. The compositions include lysates or cell wall extracts of one or more gram positive bacteria, exhibit particular activity against hepatitis C virus (HCV), and may be useful in treating those infected with HCV as well as other hepatic diseases or disorders. Also described are methods of treating a hepatic disease or disorder by administering a therapeutically effective amount of at least one therapeutically active agent capable of upregulating or downregulating the Complement system pathway, wherein the therapeutically active agent enhances the formation of one or more convertase enzymes.

4 Claims, 6 Drawing Sheets

(56) References Cited

FOREIGN PATENT DOCUMENTS

| | | |
|---|---|---|
| JP | H09301877 | 11/1997 |
| JP | H1086 | 1/1998 |
| JP | 2000004830 | 1/2000 |
| JP | 2002332242 | 11/2002 |
| JP | 2005237328 | 2/2004 |
| JP | 2005247780 | 9/2005 |
| JP | 2006507362 | 3/2006 |
| JP | 2009280606 | 12/2009 |
| JP | 2010504278 | 2/2010 |
| JP | 201168643 | 4/2011 |
| JP | 2011516521 | 5/2011 |
| JP | 2012502026 | 1/2012 |
| KR | 10-2010-0008356 A | 1/2010 |
| WO | WO 98/40100 | 9/1998 |
| WO | 2003015711 | 2/2003 |
| WO | 2003026688 | 4/2003 |
| WO | WO 2004037182 | 5/2004 |
| WO | 2007013613 | 2/2007 |
| WO | 2008000783 | 1/2008 |
| WO | 2009124954 | 10/2009 |
| WO | 2010001509 | 1/2010 |
| WO | 2010027344 | 3/2010 |
| WO | WO 2010144943 | 8/2011 |
| WO | 2011151431 | 12/2011 |
| WO | 2013109635 | 7/2013 |
| WO | WO2014/047588 | 3/2014 |

OTHER PUBLICATIONS

Lecat et al., "The protein Nod2: an innate receptor more complex than previously assumed," Biochem Pharmacol. 80 (12):2021-31 (2010).

Mikelsaar et al., "Lactobacillus fermentum ME-3—an antimicrobial and antioxidative probiotic," Microb Ecol Health Dis. 21(1):1-27 (2009).

Mohammadi et al., "Effects of Probiotics on Biomarkers of Oxidative Stress and Inflammatory Factors in Petrochemical Workers: A Randomized, Double-blind, Placebo-controlled Trial," Int J Prev Med. 2015; 6:82 (2015).

Testro et al., "Toll-like receptors and their role in gastrointestinal disease," J Gastroenterol Hepatol. 24(6):943-54 (2009).

Tran et al., "Immune response following vaccination against Salmonella enteritidis using 2 commercial bacterins in laying hens," Canadian Journal of Veterinary Research, 74(3)185-192(8) (2010).

Ayers et al., "Ability of Streptococci to survive pasteurization," Journal of Agricultural Research, vol. 2, No. 4, p. 321-330 (1914).

Chapot-Chartier et al., "Cell wall structure and function in lactic acid bacteria," Microb Cell Fact. 13 Suppl 1:S9 (2014).

Ragland et al., "From bacterial killing to immune modulation: Recent insights into the functions of lysozyme," PLoS Pathog. 13(9) (2017).

Eckner et al., "Potential for the Low-Temperature Pasteurization of Dairy Fluids Using Membrane Processing," Journal of Food Protection, vol. 54, No. 10, pp. 793-797 (1991).

Corzo, "Time, the forgotten dimension of ligand binding teaching," Biochem Mol Biol Educ 34(6):413-6 (2006).

U.S. Department of Health and Human Services "Grade "A" Pasteurized Milk Ordinance," 2009 Revision (p. 1-382).

Vorobjeva, "Propionibacteria," Springer Science & Business Media, p. 149 (1999).

Wikipedia: "Pasteurization," retrieved from the Internet:URL:https://en.wikipedia.org/wiki/Pasteurization [retrieved on Jul. 26, 2018] (pp. 1-11).

Adamberg et al., "The effect of temperature and pH on the growth of lactic acid bacteria: a pH-auxostat study," Int J Food Microbiol. 85(1-2):171-83 (2003).

Coakley et al., "Conjugated linoleic acid biosynthesis by human derived Bifidobacterium species," Journal of Applied Microbiology 94: 138-145 (2003).

Zufall et al., "The Biological Impact of Flash Pasteurization Over a Wide Temperature Interval," Journal of The Institute of Brewing 106(3): 163-167. (2000).

Bartlett et al., "Understanding the Oral Mucosal Absorption and Resulting Clinical Pharmacokinetics of Asenapine," AAPS PharmSciTech, vol. 13, No. 4 (2012).

Inagawa et al., "Oral administration of lipopolysaccharides for the prevention of various diseases: benefit and usefulness," Anticancer Res., 31(7):12431-6 (2011).

Ivanov et al., "Structure, design, and synthesis of immunoactive peptides," Pure & Appl. Chem., vol. 59, No. 3, pp. 317-324 (1987).

Kullisaar et al., "Two antioxidative lactobacilli strains as promising probiotics," Int J Food Microbiol. 72(3):1215-24 (2002).

Kullisaar et al., "Antioxidative probiotic fermented goats' milk decreases oxidative stress-mediated atherogenicity in human subjects," Br J Nutr.90(2):449-56 (2003).

Meshcheryakova et al., "Evidence for correlation between the intensities of adjuvant effects and NOD2 activation by monomeric, dimeric and lipophylic derivatives of N-acetylglucosaminyl-N-acetylmuramyl peptides," Vaccine 25 (23):14515-20 (2007).

Namba et al., "Effect of oral administration of lysozyme or digested bacterial cell walls on immunostimulation in guinea pigs," Infect Immun. Feb.;31(2):580-3 (1981).

Narang et al., "Sublingual mucosa as a route for systemic drug delivery," International Journal of Pharmacy and Pharmaceutical Sciences 3:18-22 (2001).

Salazar et al., "Enzymatic lysis of microbial cells," Biotechnol Lett., 29(7):985-94 (2007).

Sasmaz et al., "Rubella seroprevalence in women in the reproductive period, Mersin, Turkey," Vaccine. 25(5):912-7 (2006).

Schroder et al., "Lipoteichoic acid (LTA) of Streptococcus pneumoniae and Staphylococcus aureus activates immune cells via Toll-like receptor (TLR)-2, lipopolysaccharide-binding protein (LBP), and CD14, whereas TLR-4 and MD-2 are not involved," J Biol Chem. 278(18):15587-94 (2003).

Seikagaku, "Structure and function of cytoplasmic pattern recognition receptor NLR," The Journal of Japanese Biochemical Society, vol. 82 (1), pp. 12-20 (2010). (English machine translation).

Takahashi et al., "Immune Response of Mice to Orally Administered Lactic Acid Bacteria," Bioscience, Biotechnology, and Biochemistry, 57:9, p. 1557-1560 (1993).

Vauterin et al. 2000 (Synopsis on the Taxonomy of the Genus Xanthomonas; The American Phytopathological Society; Pub. No. P-2000-056-010; vol. 90, No. 7, p. 677) (2000).

Yamamoto et al., "Role of Nod2 in the development of Crohn's disease," Microbes and Infection, vol. 11 (12):912-918 (2009).

Yamamoto (Ed.), "Basic Pharmaceutical Science Textbook Series 10: Immunology," H Kagakudojin Co., Ltd., Apr. 20, 2012, 1st edition, 4th issue, pp. 156-159, p. 230 (English machine translation).

Silhavy et al., "The bacterial cell envelope," Cold Spring Harb Perspect Biol., 2(5):a000414 (2010).

Konishi et al., "Increased lipid peroxidation in patients with non-alcoholic fatty liver disease and chronic hepatitis C as measured by the plasma level of 8-isoprostane," J Gastroenterol Hepatol., 21(12):1821-5 (2006).

Krieg et al., "CpG motifs in bacterial DNA trigger direct B-cell activation," Nature, vol. 374, pp. 546-549 (1995).

Kumar et al., "Cancer-preventing attributes of probiotics: an update," Int J Food Sci Nutr. 61(5):473-96 (2010).

Laman et al., "Identification of pentadecapeptide mimicking muramyl peptide," Vaccine 25(15):2900-2906 (2006).

Lipford et al., "Bacterial DNA as immune cell activator," Trends Microbiol. 6(12):496-500 (1998).

Maletzki Claudia et al. "Bacterial Immunotherapy-Antitumoral Potential of the Streptococcal Toxin Streptolysin S-," Pancreatic Cancer-Clinical Management, Prof. Sanjay Srivastava, 163-176 (2012).

Messina et al., "Stimulation of in vitro murine lymphocyte proliferation by bacterial DNA," J. Immunol. 147:1759-1764 (1991).

Peng et al., "Protective effects of Lactobacillus plantarum NDC 75017 against lipopolysaccharide-induced liver injury in mice," Inflammation 37(5):1599-607 (2014).

(56) References Cited

OTHER PUBLICATIONS

Pineda et al., "A randomized, double-blinded, placebo-controlled pilot study of probiotics in active rheumatoid arthritis," Med Sci Monit.17(6):CR347-54 (2011).
Pinegin et al., "The occurrence of natural antibodies to minimal component of bacterial cell wall (N-acetylglucosaminyl-N-acetylmuramyl dipeptide) in sera from healthy humans," Immunol Lett. 47(1-2):33-7 (1995).
Pisetsky, "The immunologic properties of DNA," J Immunol. 156(2):421-3 (1996).
Rachmilewitz et al., "Toll-like receptor signaling mediates the anti-inflammatory effects of probiotics in murine experimental colitis," Gastroenterology 126(2):520-8 (2004).
Rau, "Adalimumab (a fully human anti-tumour necrosis factor alpha monoclonal antibody) in the treatment of active rheumatoid arthritis: the initial results of five trials," Ann Rheum Dis. 61 Suppl 2:ii70-3 (2002).
Reis et al. "LPS-induced formation of immunoproteasomes: TNF-α and nitric oxide production are regulated by altered composition of proteasome-active sites," Cell Biochem Biophys 60(1-2):77-88 (2011).
Siebler et al., "Immunization with the immunoregulatory saprophytic bacterium, *Mycobacterium vaccae*, enhances fear extinction in adult male Sprague Dawley rats," 24th Annual Meeting Of The InternationalBehavioral Neuroscience Society 24:82 (2015).
Squier et al., "Lipid Content and Water Permeability of Skin and Oral Mucosa," J Invest Dermatol. 96(1):123-6 (1991).
Te et al., "Mechanism of action of ribavirin in the treatment of chronic hepatitis C," Gastroenterol. Hepatol., 3:218-225 (2007).
Tokunaga et al., "Antitumor activity of deoxyribonucleic acid fraction from *Mycobacterium bovis* BCG. I. Isolation, physicochemical characterization, and antitumor activity," J Natl Cancer Inst. 72(4):955-62 (1984).
Vollmer et al., "Immunotherapeutic applications of CpG oligodeoxynucleotide TLR9 agonists," Advanced Drug Delivery Reviews 61(3):195-204 (2009).
Weeratna et al., "Potential use of CpG ODN for cancer immunotherapy. 18-20Update on cancer therapeutic," Update on Cancer Therapeutics 1(1):49-58 (2006).
Yi, et al., "CpG oligodeoxyribonucleotides rescue mature spleen B cells from spontaneous apoptosis and promote cell cycle entry," J Immunol. 160(12):5898-906 (1998).
Zhang et al., "CpG ODN pretreatment attenuates concanavalin A-induced hepatitis in mice," Int Immunopharmacol (1):79-85 (2010).
Zimmerman et al., "Post-traumatic anxiety associates with failure of the innate immune receptor TLR9 to evade the pro-inflammatory NFkB pathway," Transl Psychiatry 2(2): e78 (2012).
Zou et al. "An APAF-1 cytochrome c multimeric complex is a functional apoptosome that activates procaspase-9," J Biol Chem. 274(17):11549-56 (1999).
Zuezem et al., "Peginterferon alfa-2a in patients with chronic hepatitis," N Engl J Med. 343(23):1666-72 (2000).
International Preliminary Report on Patentability corresponding to Application No. PCT/US2013/021752; dated May 15, 2013 pp. 1-7.
International Search Report for corresponding International patent application No. PCT/US 2013/061236, dated Jan. 16, 2014, pp. 1-9.
International Preliminary Report on Patentability corresponding to Application No. PCT/US 2013/061236; dated Mar. 24, 2015 pp. 1-12.
Written Opinion for corresponding International patent application No. PCT/US 2013/061236; dated Dec. 12, 2013, pp. 1-11.
International Search Report and Written Opinion for corresponding International patent application No. PCT/US2016/061247, dated Jan. 26, 2017, pp. 1-16.
International Search Report for corresponding International patent application No. PCT/US2013/021752, dated May 15, 2013.
Written Opinion for corresponding International patent application No. PCT/US2013/021752, dated May 15, 2013.

Krieg, "Mechanisms and applications of immune stimulatory CpG oligodeoxynucleotides," Biochim. Biophys. Acta, 1489: 107-116(1999).
Tokunaga et al., "A synthetic single-stranded DNA, poly(dG,dC), induces interferon-alpha/beta and -gamma, augments natural killer activity, and suppresses tumor growth," Jpn. J. Cancer Res. 79:682-686 (1988).
Hu et al., "WD-40 repeat region regulates Apaf-1 self-association and procaspase-9 activation," J Biol Chem. 273 (50):33489-94 (1998).
Iliev et al., "Strong immunostimulation in murine immune cells by Lactobacillus rhamnosus GG DNA containing novel bligodeoxynucleotide pattern" Cell Microbiol. 7(3):403-14 (2005).
Inohara et al., "Nodi, an Apaf-1-like activator of caspase-9 and nuclear factor-kappaB," J Biol Chem. 274 (21):14560-7 (1999).
Kim et al., "Probiotic genomic DNA reduces the production of pro-inflammatory cytokine tumor necrosis factor-alpha," FEMS Microbiol Lett.328(1):13-9 (2012).
Kozlov et al., Effect on human complement of blastolysin and the glycopeptide (MDP and GMDP) and carbohydrate fragments of peptidoglycans, Bioorg Khim. 11(11):1510-8 (1985).
Kerkmann et al., "Spontaneous formation of nucleic acid-based nanoparticles is responsible for high interferon-alpha induction by CpG-A in plasmacytoid dendritic cells," J Biol Chem. 280(9):8086-93 (2005).
Krieg, "Toll-like receptor 9 (TLR9) agonists in the treatment of cancer," Oncogene 27, 161-167 (2008).
Krieg, "Leukocyte Stimulation by Oligodeoxynucleotides," Applied Oligonucleotide Technology, C. A. Stein and A. M. Krieg, (Eds.), John Wiley and Sons, Inc., New York, N.Y., pp. 431-448 (1998).
International Preliminary Report on Patentability corresponding to Application No. PCT/US2016/061247, dated May 15, 2018, pp. 1-10.
"Fundamentals of Freeze-Drying," Pharm. Biotechnol., 14:281-360 (2002).
"Nitric oxide synthesis protects against oxidative stress: *Bacillus subtilis* Bacterium". Online:http://www.asknature.org/strategy/2a2bf810dc95e1eebc2d1d1055fba0ec#.UxV6XfldVIF.
Becker, "CpG ODNs treatments of HIV-1 infected patients may cause the decline of transmission in high risk populations—a review, hypothesis and implications," Virus Genes 30(2):251-66 (2005).
Beutler et al., "Synergy between TLR2 and TLR4: a safety mechanism," Blood Cells Mol Dis. 27(4):728-30. (2001).
Bressanelli et al., "Structural Analysis of the Hepatitis C Virus RNA Polymerase in Complex with Ribonucleotides," Journal of Virology 76(7):3482-3492 (2002).
Ceprnja et al. "Oxidative Stress Markers in patients with post-traumatic stress disorder."Collegium Antropologicum,"" 35(4):1155-60 (2011).
Forsyth et al., "Lactobacillus GG treatment ameliorates alcohol-induced intestinal oxidative stress, gutleakiness, and liver injury in a rat model of alcoholic steatohepatitis," Alcohol 43(2): 163-172 (2009).
Fukata et al., "Toll-like receptors (TLRs) and Nod-like receptors (NLRs) in inflammatory disorders," Seminars in Immunology 21:242-253 (2009).
Galey et al., "The in vitro permeability of skin and buccal mucosa to selected drugs and tritiated water," J Invest Dermatol. 67(6):713-7 (1976).
Galigniana et al. "Regulation of the glucocorticoid response to stress-relateddisorders by the Hsp90-binding Immunophilin FKBP51," Journal of Neurochemistry 122:4-18 (2012).
Golovina et al., "Specific binding of glucosaminylmuramyl peptides to histones," FEBS Lett. 454(1-2):152-6 (1999).
Hacker et al., "CpG-DNA-specific activation of antigen-presenting cells requires stress kinase activity and is preceded by non-specific endocytosis and endosomal maturation," EMBO J.17(21):6230-40 (1998).

(56) References Cited

OTHER PUBLICATIONS

Hartmann et al., "CpG DNA: a potent signal for growth, activation, and maturation of human dendritic cells," Proc Natl Acad Sci USA 96(16):9305-10 (1999).

* cited by examiner

Human TLR/NLR Ligand Screening

Screening #1

| TLR/NLR Cell Line | No Ligand | Lysate 1/100 | Control + |
|---|---|---|---|
| hTLR2 | 0.114 | 2.188 | 2.052 |
| hTLR3 | 0.130 | 0.166 | 2.438 |
| hTLR4(MD2-CD14) | 0.183 | 0.399 | 1.900 |
| hTLR5 | 0.099 | 0.126 | 2.392 |
| hTLR7 | 0.161 | 0.185 | 2.119 |
| hTLR8 | 0.082 | 0.084 | 2.237 |
| hTLR9 | 0.153 | 0.184 | 1.984 |
| hNOD1 | 0.068 | 0.057 | 1.736 |
| hNOD2 | 0.159 | 1.504 | 1.326 |

Screening #2

| TLR/NLR Cell Line | No Ligand | Lysate 1/100 | Control + |
|---|---|---|---|
| hTLR2 | 0.093 | 2.173 | 2.046 |
| hTLR3 | 0.116 | 0.160 | 2.425 |
| hTLR4(MD2-CD14) | 0.140 | 0.301 | 1.848 |
| hTLR5 | 0.093 | 0.121 | 2.347 |
| hTLR7 | 0.158 | 0.160 | 2.081 |
| hTLR8 | 0.085 | 0.092 | 2.228 |
| hTLR9 | 0.144 | 0.186 | 2.083 |
| hNOD1 | 0.070 | 0.058 | 1.765 |
| hNOD2 | 0.172 | 1.249 | 1.335 |

Screening #3

| TLR/NLR Cell Line | No Ligand | Lysate 1/100 | Control + |
|---|---|---|---|
| hTLR2 | 0.119 | 2.140 | 1.980 |
| hTLR3 | 0.123 | 0.141 | 2.441 |
| hTLR4(MD2-CD14) | 0.135 | 0.302 | 1.870 |
| hTLR5 | 0.093 | 0.120 | 2.333 |
| hTLR7 | 0.148 | 0.138 | 2.003 |
| hTLR8 | 0.083 | 0.073 | 2.158 |
| hTLR9 | 0.152 | 0.169 | 1.954 |
| hNOD1 | 0.069 | 0.062 | 1.791 |
| hNOD2 | 0.170 | 1.597 | 1.321 |

FIG. 5

Screening #1

| Control Cell Line | No Ligand | Lysate 1/100 | TNFa |
|---|---|---|---|
| HEK293/Null1 | 0.070 | 0.083 | 1.962 |
| HEK293/Null-k | 0.133 | 0.112 | 1.820 |
| HEK293/Null2 | 0.097 | 0.081 | 1.607 |

Screening #2

| Control Cell Line | No Ligand | Lysate 1/100 | TNFa |
|---|---|---|---|
| HEK293/Null1 | 0.070 | 0.089 | 1.961 |
| HEK293/Null-k | 0.130 | 0.112 | 1.778 |
| HEK293/Null2 | 0.097 | 0.078 | 1.619 |

Screening #3

| Control Cell Line | No Ligand | Lysate 1/100 | TNFa |
|---|---|---|---|
| HEK293/Null1 | 0.068 | 0.069 | 1.985 |
| HEK293/Null-k | 0.129 | 0.199 | 1.809 |
| HEK293/Null2 | 0.099 | 0.086 | 1.636 |

FIG. 6

COMPOSITIONS AND METHODS FOR THE TREATMENT OF HEPATIC DISEASES AND DISORDERS

CROSS REFERENCE TO RELATED APPLICATIONS

This application is a continuation of U.S. application Ser. No. 15/626,055, filed Jun. 16, 2017, which is a continuation of U.S. application Ser. No. 13/743,194, filed Jan. 16, 2013, now U.S. Pat. No. 9,713,630, which claims the benefit of U.S. Provisional Application No. 61/586,975, filed Jan. 16, 2012, the disclosures of each of which are incorporated by reference herein in their entireties.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The inventions disclosed and taught herein relate generally to compositions for the therapeutic treatment of hepatic disorders, and more specifically are related to compositions and methods for the treatment of patients suffering from hepatitis, particularly hepatitis C, via compositions that act on the Complement Alternative Pathway.

Description of the Related Art

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma [Lauer, G. M., et al., N. Engl. J. Med., Vol. 345: pp. 41-52 (2001)].

HCV is classified as a positive-stranded RNA virus. Based on a comparison of the deduced amino acid sequence and the extensive similarity in the 5'-untranslated region, HCV has been classified as a separate genus within the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. Details of the HCV NS5B protein are described in detail in a variety of articles [see, e.g., Bressanelli, S., et al., Journal of Virology, Vol. 76(7), pp. 3482-3492 (2002); and, Defrancesco, et al., Clinics in Liver Disease, Vol. 7, pp. 211-242 (2003)).

Currently, one of the most effective HCV therapies employs a combination of alpha-interferon and ribavirin, leading to sustained efficacy in 40% of patients [Poynard, T., et al., Lancet, Vol. 352: pp. 1426-1432 (1998)]. Recent clinical results demonstrate that pegylated alpha-interferon is superior to unmodified alpha-interferon as monotherapy [Zeuzem, S. et al., N. Engl. J. Med., Vol. 343: pp. 1666-1672 (2000)]. However, even with experimental therapeutic regimens involving combinations of pegylated alpha-interferon and ribavirin, a substantial fraction of patients do not have a sustained reduction in viral load.

HCV-796, an HCV NS5B inhibitor, and related compounds of this class, have been reported to have an ability to reduce HCV RNA levels in patients, as described in U.S. Pat. No. 7,265,152. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens.

The hepatitis B virus (HBV) is a DNA virus that belongs to the Hepadnaviridae family of viruses. HBV causes hepatitis B in humans. It is estimated that 2 billion people have been infected (1 out of 3 people) in the world. About 350 million people remain chronically infected and an estimated 1 million people die each year from hepatitis B and its complications. HBV can cause lifelong infection, cirrhosis of the liver, liver cancer, liver failure, and death. The virus is transmitted through blood and bodily fluids. This can occur through direct blood-to-blood contact, unprotected sex, use of unsterile needles, and from an infected woman to her newborn during the delivery process. Most healthy adults (90%) who are infected will recover and develop protective antibodies against future hepatitis B infections. A small number (5-10%) will be unable to get rid of the virus and will develop chronic infections while 90% of infants and up to 50% of young children develop chronic infections when infected with the virus. Alpha-interferon is the most frequent type of treatment used. Significant side effects are related to this treatment including flu-like symptoms, depression, rashes, other reactions and abnormal blood counts. Another treatment option includes 3TC which also has many side effects associated with its use. In the last few years, there has been an increasing number of reports showing that patients treated with 3TC are developing resistant strains of HBV. This is especially problematic in the population of patients who are co-infected with HBV and HIV.

Hepatitis C virus (HCV) infection is the most common chronic blood-borne infection in the United States where the number of infected patients likely exceeds 4 million. This common viral infection is a leading cause of cirrhosis and liver cancer, and is now the leading reason for liver transplantation in the United States. Recovery from infection is uncommon, and about 85 percent of infected patients become chronic carriers of the virus and 10 to 20 percent develop cirrhosis. It is estimated that there are currently 170 million people worldwide who are chronic carriers. According to the Centers for Disease Control and Prevention, chronic hepatitis C causes between 8,000 and 10,000 deaths and leads to about 1,000 liver transplants in the United States alone each year. There is no vaccine currently available for hepatitis C. Prolonged therapy with interferon alpha, or the combination of interferon with Ribavirin, is effective in only about 40 percent of patients and often causes significant side effects in the patient.

Today, the therapeutic outlook for viral infections in general is not favorable. In general, therapies for viruses have mediocre efficacies and are associated with strong side effects which either prevent the administration of an effective dosage or prevent long term treatment.

In the case of herpesviridae, there are five major treatments currently approved for use in the clinic: idoxuridine, vidarabine, acyclovir, foscarnet and ganciclovir. While having limited efficacy, these treatments are also fraught with side effects. Allergic reactions have been reported in 35% of patients treated with idoxuridine, vidarabine can result in gastrointestinal disturbances in 15% of patients and acyclovir, foscarnet and ganciclovir, being nucleoside analogs, affect DNA replication in host cells. In the case of ganciclovir, neutropenia and thrombocytopenia are reported in 40% of patients treated with this drug.

While there are a number of different drugs currently available for the treatment of hepatitis infections, particularly hepatitis C infections, all of these are associated with side effects potent enough to require extensive supplemental medication to give patients a reasonable quality of life. The additional problem of drug resistant strains found in herpesviridae infections usually requires periodic changing of the treatment cocktail and in some cases, makes the infection extremely difficult to treat.

Clearly, there is a need for improved therapies to treat patients suffering from such viral disorders. The present disclosure provides technical advantages over what has generally been used in the previous approaches. For example, the compositions are novel and are effective against at least hepatitis C, and likely other hepatitis viruses, including hepatitis B. Additionally, the compounds provide advantages for pharmaceutical uses, for example, with regard to one or more of their mechanism of action, binding, inhibition efficacy, target selectivity, solubility, safety profiles, and/or bioavailability.

The inventions disclosed and taught herein are directed to compositions and methods for the treatment of hepatitis viral infections in subjects in need of such treatment, using an oral formulation comprising at least a fraction of a gram positive bacteria.

BRIEF SUMMARY OF THE INVENTION

Applicants have created compositions, methods and formulations useful in the therapeutic treatment of a subject suffering from a hepatic disease or disorder, including infections such as viral infections such as hepatitis A, hepatitis B, or hepatitis C, iatrogenic disorders, cholestatic disorders, hereditary disorders, sarcoidosis, organ transplant, and the like.

In accordance with a first embodiment of the present disclosure, a composition for the delivery of a therapeutic agent across the mucosa of a subject for the treatment of a hepatitis disorder is described, wherein the composition comprises (a) a lysate or cell wall extract from a gram-positive bacteria, or a pharmaceutically acceptable salt thereof; (b) a promoter; and (c) an optional carrier, wherein the cell wall lysate is present in an amount effective to treat a hepatitis disorder. In accordance with further aspects of this embodiment, the composition further comprises one or more control release agents.

In yet another aspect of this embodiment, the gram positive bacteria is selected from the group consisting of *Streptococcus thermophilus*, *Bifidobacterium infantis*, *Bifidobacterium longum*, *Bifidobacterium breve*, *Lactobacillus acidophilus*, *Lactobacillus plantarum*, *Lactobacillus delbrueckii* subsp. *Bulgaricus*, *Streptococcus thermophilus*, *Bifidobacterium lactis*, *Bifidobacterium breve*, *Lactobacillus acidophilus*, *Lactobacillus plantarum*, *Lactobacillus casei* (including *Lactobacillus casei* ssp. *Rhamnosus*), *Lactobacillus rhamnosus*, and *Lactobacillus helveticus*, and combinations thereof.

In another embodiment of this disclosure, a method of treating hepatitis C infection in a subject is described, the method comprising administering a therapeutically effective amount of a therapeutic composition to a subject in need of such treatment, wherein the therapeutic composition comprises (a) a lysate or cell wall extract from a gram-positive bacteria, or a pharmaceutically acceptable salt thereof; and (b) a promoter, wherein the cell wall lysate is present in an amount effective to treat a hepatitis disorder.

In accordance with a further embodiment of the present disclosure, a method of treating a hepatitis disease in a subject is described, the method comprising administering to a subject in need thereof a therapeutically effective amount of at least one therapeutically active agent capable of upregulating or downregulating the Complement system pathway, wherein the therapeutically active agent enhances the formation of one or more convertase enzymes. In a further aspect of this embodiment, the at least one therapeutically active agent is a gram positive bacteria selected from the *Lactobacillus* family, *Streptococcus* family, or *Bifidobacterium* family, or a biologically active fragment or variant thereof.

In accordance with yet another embodiment of the present disclosure, a method of reducing or inhibiting Toll Like Receptor (TLR)-induced inflammation in a subject is described, the method comprising administering to a subject in need thereof an effective amount of a composition comprising (a) a lysate or cell wall extract from a gram-positive bacteria, or a pharmaceutically acceptable salt thereof; (b) a promoter; and (c) an optional carrier, wherein the cell wall lysate is present in an amount effective to treat an inflammatory disorder, thereby reducing or inhibiting Toll Like Receptor (TLR)-induced inflammation in the subject. In accordance with further aspects of this embodiment, the TLR is one or more of TLR 2, TLR 3, TLR 4, TLR 5, TLR 7, TLR 8 and TLR 9, preferably TLR 2, TLR 4 or TLR 9.

In accordance with a further embodiment of the present invention, a method of reducing or inhibiting a Nod-induced disorder in a subject is described, the method comprising the steps of administering to a subject in need thereof an effective amount of a composition comprising (a) a lysate or cell wall extract from a gram-positive bacteria, or a pharmaceutically acceptable salt thereof; (b) a promoter; and (c) an optional carrier, wherein the cell wall lysate is present in an amount effective to treat the disorder, thereby reducing or inhibiting the Nod-induced disorder in the subject. In further accordance with aspects of this embodiment, the Nod is one or more of Nod1 and Nod2. In accordance with further, select aspects, the Nod is preferably Nod2.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

FIG. 5 illustrates the results of the Human TLR/NLR Ligand screening.

FIG. 6 illustrates the results of the NF-κB Control Cell screening.

Figure 1:
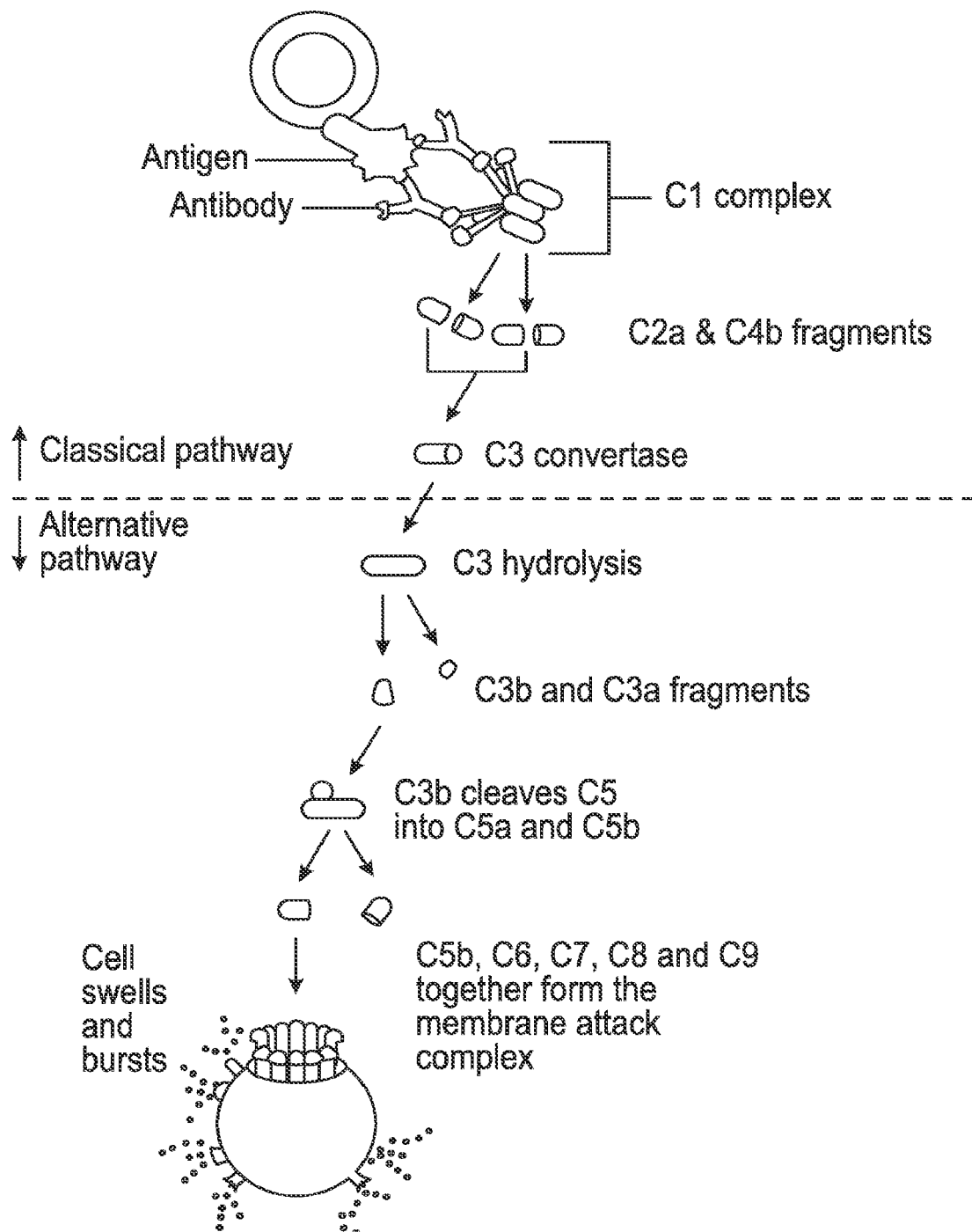
FIG. 1 illustrates a general schematic of the classical and alternative complement pathways, in accordance with mechanisms of action of the compositions of the present disclosure.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

Definitions

The following definitions are provided in order to aid those skilled in the art in understanding the detailed description of the present invention.

The phrase "pharmaceutical composition" refers to a formulation of a compound and a medium generally accepted in the art for the delivery of the biologically active compound to mammals, e.g., humans. Such a medium includes all pharmaceutically acceptable carriers, diluents or excipients therefore.

The phrase "pharmaceutically acceptable carrier, diluent or excipient" as used herein includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The term "therapeutically effective amount", as used herein, the dose administered to an animal, such as a mammal, in particular a human, should be sufficient to prevent the targeted disease or disorder, e.g., cancer, delay its onset, slow its progression, or treat the disease or disorder (e.g., reverse or negate the condition). One skilled in the art will recognize that dosage will depend upon a variety of factors including the strength of the particular composition employed, as well as the age, species, condition, and body weight of the animal. The size of the dose will also be determined by the route, timing, and frequency of administration as well as the existence, nature, and extent of any adverse side-effects that might accompany the administration of a particular composition and the desired physiological effect.

"Biological active agent", as used herein, refers to any amino acid, peptide, protein, or antibody (including chimeric, monoclonal, isolated, or humanized antibodies), natural or synthetic, which exhibits a therapeutically useful effect. Such biologically active agents may include recombinant proteins, enzymes, peptoids, or PNAs, as well as combinations of such agents.

The phrase "pharmaceutically acceptable" or "pharmacologically-acceptable" refers to compositions that do not produce an allergic or similar unexpected reaction when administered to a human or animal in a medical or veterinary setting.

The term "ligand" as used herein means a molecular group that is associated with a central metal atom. The terms bidentate (or didentate), tridentate, tetradentate, and multidentate are used to indicate the number of potential binding sites of the ligand. For example, a carboxylic acid can be a bidentate or other multidentate ligand because it has at least two binding sites, the carboxyloxygen and hydroxyloxygen. In like manner, an amide has at least two binding sites, the carboxyloxygen and the nitrogen atom. An amino sugar can have at least two binding sites and many amino sugars will have multiple binding sites including the amino nitrogen, a hydroxyloxygen, an ethereal oxygen, an aldehyde carbonyl, and/or a ketone carbonyl.

The term "amino sugar" as used herein refers to monosaccharides having one alcoholic hydroxyl group (commonly but not necessarily in the '2-position') replaced by an amino group, systematically known as x-deoxy-x-monosaccharides. By way of non-limiting example, D-glucosamine or 2-amino-2-deoxy-D-glucopyranose is an amino sugar. Other illustrative amino sugars include but are not limited to erythrosamine, threosamine, ribosamine, arabinosamine, xylosamine, lyxosamine, allosamine, altrosamine, glucosamine, mannosamine, idosamine, galactosamine, talosamine, and their derivatives, all of which are suitable for use within the compositions of the present disclosure. The amino sugars include both aldose and ketose sugars. Additionally, the amino sugars may be of a straight-chain structure; however, the aldehyde or ketone group of the amino sugar may react with a hydroxyl group on a different carbon atom to form a hemiacetal or hemiketal, in which case there is an oxygen bridge between the two carbon atoms, forming a heterocyclic ring. Amino sugar rings with five and six atoms are called furanose and pyranose forms, respectively and exist in equilibrium with their corresponding straight-chain form. It should be noted that the ring form has one more optically active carbon than the straight-chain form, and so has both an α- and a β-form, which interconvert in equilibrium. The term "amino sugar" also means glycosylamines, amino sugars where the nitrogen is substituted with a functional group other than H. Illustrative, non-limiting examples of glycosylamines include N-acetylglucosamine (NAG) and N-methylglucosamine.

The term "glycosaminoglycans" as used herein means any of any of a group of polysaccharides that contain amino sugars. Glycosaminoglycans can also form complexes with proteins.

The terms "hydrate" or "n-hydrate" as used herein means a molecular entity with some degree of hydration, where n is an integer representing the number of waters of hydration, e.g., monohydrate, dihydrate, trihydrate, tetrahydrate, pentahydrate, hexahydrate, septahydrate, octahydrate, nonahydrate, etc.

The compositions of the present invention may be prepared for pharmaceutical administration by methods and with excipients generally known in the art, such as described in *Remington's Pharmaceutical Sciences* [Troy, David B., Ed.; Lippincott, Williams and Wilkins; 21st Edition, (2005)].

"Treating" or "treatment" as used herein covers the treatment of the disease or condition of interest, e.g., tissue injury, in a mammal, preferably a human, having the disease or condition of interest, as well as prophylactic, or suppressive measures for the disease or disorder and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition. Thus, for example, the term "treatment" includes the administration of an agent prior to or following the onset of a disease or disorder, thereby preventing or removing all signs of the disease or disorder. As another example, administration of the agent after clinical manifestation of the disease to combat the symptoms of the disease comprises "treatment" of the disease. Further, administration of the agent after onset and after clinical symptoms have developed where administration affects clinical parameters of the disease or disorder, such as the degree of tissue injury or the amelioration of the disease, comprises "treatment" of the disease.

The term "nitric oxide releasing" or "nitric oxide donating" refers to methods of donating, releasing and/or directly or indirectly transferring any of the three redox forms of nitrogen monoxide ($NO^+$, $NO^-$, $NO^*$), such that the biological activity of the nitrogen monoxide species is expressed at the intended site of action.

The term "nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo and/or are oxidized to produce nitric oxide and/or are substrates for nitric oxide synthase and/or cytochrome P450. "NO donor" also includes compounds that are precursors of L-arginine, inhibitors of the enzyme arginase and nitric oxide mediators.

The phrase "in need of treatment" includes mammals, such as humans, or animals, already having the disease or disorder, including those in which the disease or disorder is to be prevented.

As used herein, the terms "disease," "disorder," and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As used herein, the expressions "agent", "composition", and "antagonist" are used interchangeably within the scope of the present disclosure, and are meant to include any molecule or substance which results in a therapeutic effect when administered to a subject suffering from a lymphatic disorder.

The term "iatrogenic disorder", as used herein, refers to those disorders induced by exposure to a therapeutic compound intended to treat some other disorder. Examples of drug induced liver diseases or disorders include, for example, chronic active hepatitis associated with the administration of Amineptine, Clometacine, Dantrolene, Diclofenac, and Fenofibrate to name a few; chronic cholestasis associated with the administration of Aceprometazine, Ajmaline and related drugs, Amitryptyline, and Ampicillin to name but a few; or hepatic granulomas associated with the administration of Allopurinal, Aspirin, and Diazepam. In this context, reference can be made to Tables 14.8, 14.10 and 14.11 of "MacSween's Pathology of the Liver, 5th Ed." [(Burt, Portman, and Ferrell, Eds.), Churchill Livingstone (2007), in Ch. 14, "Hepatic Injury Due to Drugs, Chemicals and Toxins" by Lewis, J. H. and Kleiner, D. E., pp. 649-759], the disclosure of which is incorporated in relevant part herein by reference.

The term "water-insoluble" encompasses the terms sparingly water-soluble, slightly or very slightly water-soluble, as well as practically or totally water-insoluble compounds [see, *Remington: The Science and Practice of Pharmacy*, vol. I, 194-195 (Gennaro, ed., 1995)]. As used herein, a compound is water-insoluble for the purposes of this invention if it requires at least 30 parts solvent (e.g., water or saline) to dissolve one part solute (Id.). In accordance with the present disclosure, the term "water-insoluble" also encompasses oil- or lipid-soluble, as well as substantially oil- or lipid soluble.

Except as otherwise specifically provided or clear from the context, the term "compounds" of the invention should be construed as including the "pharmaceutically acceptable salts" thereof as appropriate (which expression has been eliminated in certain instances for the sake of brevity).

As used herein, the term "%" when used without qualification (as with w/v, v/v, or w/w) means % weight-in-volume for solutions of solids in liquids (w/v), % weight-in-volume for solutions of gases in liquids (w/v), % volume-in-volume for solutions of liquids in liquids (v/v) and weight-in-weight for mixtures of solids and semisolids (w/w), such as described in *Remington's Pharmaceutical Sciences* [Troy, David B., Ed.; Lippincott, Williams and Wilkins; 21st Edition, (2005)].

The terms "patient" and "subject", as used herein, are used interchangeably and refer generally to a mammal, and more particularly to human, ape, monkey, rat, pig, dog, rabbit, cat, cow, horse, mouse, sheep and goat. In accordance with this definition, lung surfaces or membranes described and referenced in accordance with this disclosure refer to those of a mammal, preferably a human or an animal test subject.

As used herein, "enhancing" and/or "providing relief" with respect to the therapeutic compositions disclosed, means that the administration of the referenced composition to a subject provides an immediate and/or extended alleviation, amelioration, inhibition, or mitigation of one or more symptoms of a hepatitis disorder to the subject mammal.

The term "drug" as used in conjunction with the present disclosure means any compound which is biologically active, e.g., exhibits or is capable of exhibiting a therapeutic or prophylactic effect in vivo, or a biological effect in vitro.

As used herein, the term "oral mucosa" refers to the mucous matrix that covers all structures inside the oral cavity except the teeth. The oral mucosa generally varies in color from pink to brownish purple depending on an individual's skin color. The structure of the oral mucosa varies depending on its location in the oral cavity and the function of that area. For example, the mucosa lining the cheeks is not designed to withstand the heavy force of mastication while the masticatory mucosa covering the jaws is structured to withstand the forces of mastication. A specialized mucosa that includes taste buds covers the tongue. Example of oral mucosa tissue include, but are not limited to, palate tissue, gingiva tissue, buccal mucosa tissue, tongue tissue, and floor of the mouth tissue.

The term "controlled drug-delivery system", or "DDS", as used herein, refers to a formulation that controls the rate and period of therapeutic agent/drug delivery (i.e., time-release dosage), targets specific areas of the subjects body, and are designed to maintain therapeutic levels during the desired treatment period, such as described by M. Vallet-Regi [*Chem. Eur. J.*, Vol. 12, pp. 5934-5943 (2006)].

The term "bioavailability" refers to the rate and/or extent to which a drug is absorbed or becomes available to the treatment site in the body.

The term "administering" as used herein refers to administration of the compositions of the present invention to the mucous membranes of the oral cavity (i.e., oral mucosa). Examples of suitable sites of administration within the oral mucosa include, without limitation, the mucous membranes of the floor of the mouth (sublingual mucosa), the cheeks (buccal mucosa), the gums (gingival mucosa), the roof of the mouth (palatal mucosa), the lining of the lips, and combinations thereof. Preferably, the compositions of the present invention are administered to the sublingual mucosa, buccal mucosa, or a combination thereof.

The term "functionally equivalent variants" as used herein refers to microorganisms which essentially have the same properties and functions as the original microorganisms. Such variants can be formed arbitrarily, for example, by UV irradiation, or other mutagenesis techniques known to a person skilled in the art, as well as taxonomical name changes, such as a change in the Bifidobacteria genus.

As used herein, the term "lysing," with reference to a cell suspension, refers to rupturing the cell walls and/or cell membranes, cellular components, organelles of at least a portion of the cells such that at least part of the contents, e.g. biological molecules of the cells are released. In certain embodiments of the method of the present invention, at least a portion of the biological material is lysed to form a lysate. Without being bound by any particular theory of operation, the biological sample lyses under physico-chemical forces created by the combination of the appropriate solvent environment, along with pressure and either heat or cavitation, or a combination of the two. Biological molecules that are released upon lysing include nucleic acids, carbohydrates, amino acids, proteins, peptides, DNA, RNA, complex sugars (oligosaccharides), peptidoglycans, and any combination thereof. Biological samples are typically aqueous, which means they contain an effective amount of water molecules to cause them to be in the liquid state.

The term "lysis" as used herein refers to the rupturing of a cell membrane or cell wall (e.g., by digestion using enzymes or other appropriate materials) and release of the cytoplasm from the cell. As used herein, the term "lysate" refers to the material produced by the destructive process of lysis, specifically a liquefied phase with lysed cell debris (e.g., ruptured cell walls and/or cell membranes) and DNA.

As used herein, the term "lysate" refers to the products of lysing biological material, for example, the biological molecules that are released as listed above. Although most lysates will be readily soluble in the biological sample fluid, certain lysate portions, such as hydrophobic components, may require additional steps to ensure at least a portion of the lysate is solubilized. Examples of additional steps for ensuring solubilization of the lysates include a suitable surfactant (or dehydrant), such as sodium dodecyl sulfate (SDS), which is typically included in the buffer, or any combination thereof. Lysate solubilization may also be assisted using vigorous mixing, shearing, heating in surfactant, cavitation, bead beating, boiling, degassing, or any combination thereof.

The term "cell", as used herein, is intended to encompass prokaryotic cells, eukaryotic cells, phage particles, and organelles.

As used herein, the term "chemotherapeutic agent" means a cytotoxic compound which inhibits the proliferation of tumor or cancers cells in a subject. Chemotherapeutic agents may, in some circumstances, have a cytotoxic effect on normal (non-cancerous and non-tumor) cells in a patient.

The term "downregulation" as used herein, refers to the process by which a cell decreases the quantity of a cellular component, such as RNA or a protein, in response to an external variable, such as a therapeutic agent.

The term "upregulation" as used herein refers to the process by which a cell increases the quantity of a cellular component, such as RNA or a protein, in response to an external variable, such as a therapeutic agent.

DETAILED DESCRIPTION

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Applicants have created compositions and methods for the therapeutic treatment of hepatic disorders, including hepatitis C and hepatitis B, wherein the compositions can be delivered orally to the subject and exhibit little to no detrimental side effect.

Applicant has also created methods for modulating (e.g., controlling, such as by up- or down-regulating) the alternative pathway (AP) of the Complement System, using the therapeutically active compositions of the present disclosure.

A. Compositions.

The therapeutically active compositions of the present disclosure include a natural, non-synthetic biologically active agent, preferably one or more cell wall fractions of one or more gram positive bacteria, such as in the form of a lysate; a promoter; and optionally, one or more other additives, including control-release ingredients, so as to allow the composition to be absorbed into, or interact with, a mucosal wall of the subject in need of therapy.

According to the present invention, the active therapeutic agent is a mixture of one or more lysate or cell wall fraction of a gram-positive bacteria, in an amount ranging from about 1 mg/kg to about 100 mg/kg, as required depending upon the specific therapeutic application. In accordance with the present disclosure, the lysate or cell wall fraction of a gram-positive bacteria is from the group of gram-positive bacteria selected from the group consisting of *Lactobacillus acidophilus, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus delbrueckii* subsp. *bulgaricus, Lactobacillus delbrueckii* subsp. *lactis, Lactobacillus helveticus, Lactobacillus jensenii, Lactobacillus leichmanmii, Lactobacillus minutus, Lactobacillus paracasei, Lactobacillus plantarum, Lactobacillus rhamnosus, Lactobacillus rogosae, Lactobacillus salivarius, Lactobacillus sporogenes* (also known as *Bacillus coagulans*), *Lactobacillus brevis, Lactobacillus gasseri, Lactobacillus fermentum, Bifidobacterium adolescentis, Bifidobacterium animalis* (especially *B. animalis*, subspecies *animalis*), *Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium lactis* (*Bifidobacterium animalis* subsp. *lactis*), *Bifidobacterium longum, Bifidobacterium plantarum, Bifidobacterium pseudo-catenulatum, Bifidobacterium pseudo-longum, Leptococcus lactis, Streptococcus lactis* (also referred to as *Lactococcus lactis* subsp. *lactis*), *Streptococcus raffinolactis, Acidaminococcus fermenta, Cytophaga fermentans, Rhodoferax fermentans, Cellulomonas fermentans, Zymomonas mobilis,* and *Streptococcus thermophilus*, as well as functionally equivalent variants thereof, all of which are suitable for carrying out the present invention. These mixtures of well-known species can be easily prepared by any person having ordinary experience in this field.

Other species can be used, for example those disclosed in the state of the art and generally available in collections, such as the ECACC (European Collection of Cell Cultures), ASTM; and DSM.

The preferred thereapeutic active agents according to the present invention are lysates or cell wall extracts of gram-positive bacteria selected from the group consisting of the following: *Streptococcus thermophilus, Bifidobacterium animalis* (especially *B. animalis,* subspecies *animalis*), *Bifidobacterium infantis, Bifidobacterium longum, Bifidobacterium breve, Lactobacillus acidophilus, Lactobacillus plantarum, Lactobacillus casei, Lactobacillus delbrueckii* subsp. *bulgaricus, Lactococcus lactis, Bacillus coagulans* (*Lactobacillus sporogenes*), *Bifidobacterium lactis* (*Bifidobacterium animalis* subsp. *lactis*), *Bifidobacterium breve, Lactobacillus acidophilus, Lactobacillus plantarum, Lactobacillus casei, Lactobacillus rhamnosus,* and *Lactobacillus helveticus*, as well as functionally equivalent variants thereof. Some of these mixtures are commercially available in a lyophilized form.

The therapeutic compositions of the present disclosure may further and optionally comprise one or more promoters, to assist in the therapeutic delivery of the active agent across the biological membrane. Preferably, the promoter useful in accordance with the present disclosure is an amino acid, N-alkylated peptide, sugar, amino sugar or amino sugar chelate. An amino sugar chelate comprising one or more amino sugar ligands, one or more saturated hydroxylated carboxylic acid ligands, and a nutritionally acceptable metal, wherein at least one of the one or more amino sugar ligands is glucosamine, and wherein the metal is selected from the group consisting of manganese, magnesium, sodium, potassium, and zinc, and wherein the one or more saturated hydroxylated carboxylic acid ligands is gluconic acid, and wherein the glucosamine ligand to nutritionally acceptable metal ratio is 2:1, wherein the nutritionally metal is nonferrous.

In accordance with one aspect of the present disclosure, the therapeutic formulations may include one or more acetylated or deacetylated amino sugars selected from the group consisting of NAG, galactosamine, N-acetylgalactosamine, mannosamine, and N-acetylmannosamine in the form of monomers, oligomers, and/or polymers thereof including chitin, and human glucosaminoglycans, as well as derivatives thereof. The term "derivatives thereof" used herein with reference to amino sugars means derivatives of the amino sugars having the same or essentially the same ability to form cytotoxic degradation products during steriliszation. In accordance with select further aspects of the present disclosure, the promoter is a member selected from the group consisting of poly-L-lysine, glucosamine, poly-L-arginine, galactosamine, N-acetylmannosamine (NAM; N—Ac-Man), N-acetylglucosamine (NAG; N—Ac-Glc), N,N'-diacetylglucosamine (NAG-NAG; N,N'-diacetylchitobiose), N,N', N", N"'-tetraacetylglucosamine (NAG-NAG-NAG-NAG; N,N',N",N'"-tetraacetylchitotetraose), and mixtures thereof.

Optionally, and equally acceptable, the promoter may be an acylated glycosyloxy sugar or an optionally acylated oligoglycosyloxy sugar moiety of 2 to 12 α-1,2 and/or α-1,6 linked sugars, wherein the sugar(s) are selected from the group consisting of D-mannose, D-galactose, D-glucose, D-glucosamine, N-acetylglucosamine, and 6-deoxy-L-mannose, wherein an oligoglycosyloxy sugar moiety may comprise the same or different sugars.

In accordance with further aspects of the present disclosure, the therapeutic formulations of the invention may further comprise one or more additional therapeutic agents, such as the second therapeutic agents described below. The compositions will usually be supplied as part of a sterile, pharmaceutical composition that will normally include a pharmaceutically acceptable carrier. This composition, comprising additional therapeutic agents, can be in any suitable form (depending upon the desired method of administering it to a patient).

In certain aspects, the second therapeutic agent is an anti-rheumatic drug, an anti-inflammatory agent, a chemotherapeutic agent, a radiotherapeutic, an immunosuppressive agent, an interferon, an interferon-based chemotherapeutic, a different bacterial wall lysate, or a cytotoxic drug.

Anti-rheumatic drugs include, but are not limited to, auranofin, azathioprine, chloroquine, D-penicillamine, gold sodium thiomalate hydroxychloroquine, Myocrisin and sulfasalazine methotrexate.

Anti-inflammatory agents include, but are not limited to, dexamethasone, pentasa, mesalazine, asacol, codeine phosphate, benorylate, fenbufen, naprosyn, diclofenac, etodolac and indomethacin, aspirin and ibuprofen, as well as non-steroidal is anti-inflammatory agents (NSAIDS).

Chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucovorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-.alpha., Erwinia L-asparaginase, esterified estrogens, estradiol, estramustine phosphate sodium, ethidium bromide, ethinyl estradiol, etidronate, etoposide citrovorum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon .alpha.-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptopurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In yet other aspects of the disclosure, the second therapeutic agent is a TNF-α antagonist or an anti-TNF-α antibody of the disclosure. Examples of such TNF-α antagonists include, but are not limited to, soluble TNF-α receptors; etanercept (ENBREL®; Immunex) or a fragment, derivative or analog thereof; infliximab (REMICADE®; Centacor) or a derivative, analog or antigen-binding fragment thereof; IL-10, which is known to block TNF-α production via interferon-γ-activated macrophages, TNFR-IgG; the murine product TBP-1; the vaccine CytoTAb (Protherics); antisense molecule 104838 (ISIS); the peptide RDP-58 (SangStat); thalidomide (Celgene); CDC-801 (Celgene); DPC-333 (Dupont); VX-745 (Vertex); AGIX-4207 (AtheroGenics); ITF-2357 (Italfarmaco); NPI-13021-31 (Nereus); SCIO-469 (Scios); TACE targeter (Immunix/AHP); CLX-120500 (Calyx); Thiazolopyrim (Dynavax); auranofin (Ridaura) (SmithKline Beecham Pharmaceuticals); quinacrine (mepacrine dichlorohydrate); tenidap (Enablex); Melanin (Large Scale Biological); and anti-p38 MAPK agents by Uriach.

Additionally, the second therapeutic agents made from particulate cellular wall fragments of particular lactic acid bacteria (e.g., Del-Immune V®, Pure Research Products, LLC, Colorado, USA), which are intended to stimulate the immune system.

In further aspects of the present disclosure, the second therapeutic agent is rapamycin, or similar macrocyclic antibiotics. As used herein, rapamycin includes rapamycin and all analogs, derivatives and congeners thereof, and other immunophilins that possesses the same pharmacologic properties as rapamycin is including inhibition of TOR or mTOR (mammalian target of rapamycin) (e.g., acting as a TOR kinase inhibitor). Other immunosuppressives that can be used as the second therapeutic agent include but are not limited to cyclosporine, tacrolimus (FK-506), azathioprine, and mycophenolate mofetil)

Further therapeutic agents that may be combined with the first therapeutic agent alone or with the first and second thereapeutic agents also include angiogenic agents such as vascular endothelial growth factor (VEGF) and fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Rapamycin is an exemplary preferred immunosuppressive. Rapamycin is a macrocyclic triene antibiotic produced by *Streptomyces hygroscopicus* as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls. Rapamycin reduces vascular hyperplasia by antagonizing smooth muscle proliferation in response to mitogenic signals that are released during an angioplasty induced injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity.

In 1977, rapamycin was also shown to be effective as an immunosuppressant in the experimental allergic encephalomyelitis model, a model for multiple sclerosis; in the adjuvant arthritis model, a model for rheumatoid arthritis; and was shown to effectively inhibit the formation of IgE-like antibodies [Martel, R., et al., *Can. J. Physiol. Pharmacol.*, Vol. 55, 48 (1977)]. The immunosuppressive effects of rapamycin have also been disclosed in *FASEB*, 1989, 3, 3411 as has its ability to prolong survival time of organ grafts in histoincompatible rodents [Morris, R., *Med. Sci. Res.*, Vol. 17, 877 (1989)]. The ability of rapamycin to inhibit T-cell activation was disclosed by M. Strauch [*FASEB*, 1989, 3, 3411]. These and other biological effects of rapamycin are reviewed in *Transplantation Reviews*, Vol. 6, 39-87 (1992).

In another embodiment, the compositions of the present invention are in a dosage form selected from the group consisting of a lozenge, a chewing gum, a chewable tablet, and a dissolving tablet such as a slow-dissolving tablet, a quick-dissolving tablet, or a controlled-release tablet or other suitable controlled-release formulation. Preferably, the composition is a lozenge or a dissolving tablet.

In a preferred embodiment, the active agent of the present disclosure is delivered across an oral mucosa of a subject, the oral mucosa being selected from the group consisting of the sublingual mucosa, the buccal mucosa, and a combination thereof. Preferably, the composition is administered sublingually so that the active ingredient is delivered across the sublingual mucosa.

In another embodiment, the carrier is typically a solid, semi-solid, or liquid such as a binder, a gum base, or combinations thereof. Suitable binders for use in the compositions of the present invention include, without limitation, sugar alcohols such as mannitol, sorbitol, and xylitol; sugars such as lactose, dextrose, sucrose, glucose, and powdered sugar; other substances such as inositol, molasses, maltodextrin, starch, cellulose, microcrystalline cellulose, polyvinylpyrrolidone, acacia gum, guar gum, tragacanth gum, alginate, extract of Irish moss, panwar gum, ghatti gum, mucilage of isapol husks, VEEGUM®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol; and combinations thereof. Suitable gum bases for use in the compositions of the present invention include, for example, materials selected from among the many water-insoluble and saliva-insoluble gum base materials known in the art. In certain instances, the gum base comprises at least one hydrophobic polymer and at least one hydrophilic polymer. Non-limiting examples of suitable hydrophobic and hydrophilic polymers for gum bases include both natural and synthetic polymers such as elastomers, rubbers, and combinations thereof. Examples of suitable natural polymers include, without limitation, substances of plant origin such as chicle, jelutong, gutta percha, crown gum, and combinations thereof. Examples of suitable synthetic polymers include elastomers such as butadiene-styrene copolymers, isobutylene and isoprene copolymers (e.g., "butyl rubber"), polyethylene, polyisobutylene, polyvinylester (e.g., polyvinyl acetate and polyvinyl acetate phthalate), and combinations thereof. In other instances, the gum base comprises a mixture of butyl rubber (i.e., isobutylene and isoprene copolymer), polyisobutylene, and optionally, polyvinylacetate (e.g., having a molecular weight of approximately 12,000).

In yet another embodiment, the compositions of the present invention can further comprise a sweetening agent, a flavoring agent, a protecting agent, a plasticizer, a wax, an elastomeric solvent, a filler material, a preservative, or combinations thereof. In still yet another embodiment, the compositions of the present invention can further comprise a lubricating agent, a wetting agent, an emulsifying agent, a solubilizing agent, a suspending agent, a coloring agent, a disintegrating agent, or combinations thereof. In a preferred embodiment, the average particle size of the drug in the compositions described herein is about 20 microns, as compared to a typical average drug particle size of from about 75 to about 100 microns. In another preferred embodiment, the average particle size of the drug in the compositions described herein is less than or equal to the average particle size of the carrier ingredients (e.g., gum base, binders, etc.).

In one aspect of the present disclosure, the therapeutic composition may optionally include a buffer system to raise the pH of saliva to a pH of from about 8.0 to about 11, irrespective of the starting pH of saliva in the oral cavity of the subject to be treated. Suitable therapeutic agents for use in the present invention are described above. Suitable carbonate salts and bicarbonate salts for use in the buffer systems of the present invention are also described above. In certain instances, composition further comprises a non-biologic therapeutic agent, such as an NSAID.

Suitable citrate, phosphate, and borate salts include, without limitation, any salt of citric acid, phosphoric acid, or boric acid known in the art. For example, in some embodiments, the citrate salt is selected from the group consisting of sodium citrate, potassium citrate, calcium citrate, magnesium citrate, and ammonium citrate. In other embodiments, the phosphate salt is selected from the group consisting of monobasic sodium phosphate, dibasic sodium phosphate, monobasic potassium phosphate, dibasic potassium phosphate, monobasic calcium phosphate, dibasic calcium phosphate, monobasic magnesium phosphate, dibasic magnesium phosphate, monobasic ammonium phosphate, and dibasic ammonium phosphate. In yet other embodiments, the borate salt is selected from the group consisting of sodium borate, potassium borate, calcium borate, magnesium borate, and ammonium borate. In certain instances, the buffer system comprises a carbonate salt, a bicarbonate salt, and/or a citrate salt. In certain other instances, the buffer system comprises a carbonate salt, a bicarbonate salt, and/or a phosphate salt. In further instances, the buffer system comprises a carbonate salt, a bicarbonate salt, and/or a borate salt.

In addition to a buffer system comprising a carbonate salt, a bicarbonate salt, and/or a metal oxide, other buffer systems are suitable for use in the compositions of is the present invention. For example, in an alternative embodiment, the ternary buffer system comprises a carbonate salt, a bicarbonate salt, and a citrate, phosphate, or borate salt. In another alternative embodiment, the buffer system comprises a carbonate salt or a bicarbonate salt and two or more buffering agents selected from the group consisting of a metal oxide, a citrate salt, a phosphate salt, and a borate salt. In yet another alternative embodiment, the buffer system is a binary buffer system comprising a carbonate salt or a bicarbonate salt and a metal oxide. In still yet another alternative embodiment, the buffer system is a binary buffer system comprising, a carbonate salt or a bicarbonate salt and a citrate, phosphate, or borate salt. In a further alternative embodiment, the buffer system is a binary buffer system comprising a metal oxide and a citrate, phosphate, or borate salt. In still yet another alternative embodiment, the buffer system is a binary buffer system comprising a carbonate salt and a bicarbonate salt, preferably sodium carbonate and sodium bicarbonate.

In other embodiments of the invention, the gram positive bacterial lysate compositions described herein may include one or more organic nitric oxide enhancing compounds, or organic nitric oxide donors. The organic nitric oxide enhancing compounds are preferably, but not necessarily, organic compounds that form salts such as preferably organic nitrates, organic nitrites, nitrosothiols, thionitrites and heterocyclic nitric oxide donors.

In further accordance with this embodiment, the organic nitric oxide donor is a salt of an antimicrobial compound. In accordance with aspects of this embodiment, the antimicrobial compounds that can be used to form salts and thus become nitric oxide donors include but are not limited to acediasulfone, aceturate, acetyl sulfametossipirazine, acetyl sulfamethoxypyrazine, acranil, albendazole, alexidine, amatadine, ambazone, amdinocillin, p-aminosalicylic acid, p-aminosalicylic acid hydrazine, amoxicillin, ampicillin, anisomycin, apalcillin, apicyclin, apramycin, argininsa, aspoxicillin, azidamfenicol, azidocillin, azithromycin, azlocillin, bacampicillin, benzoylpas, benzyl penicillin acid, benzyl sulfamide, bicozamycin, bipenam, brodimoprim, capreomycin, carbenicillin, carbomycin, cafazedone, carindacillin, cefcapene pivoxil, cefaclor, cefadroxil, cefafroxil, cefamandole, cefatamet, cefatrizine, cefazedone, cefazolin, cefbuperazone, cefclidin, cefdinir, cefditoren, cefixime, cefmenoxime, cefmetazole, cefminox, cefodizime, cefonicid, cefoperazone, ceforanide, cefotaxime, cefotetan, cefotiam, cefoxitin, cefozopran, cefpimizole, cefpiramide, cefpirome, cefpodoxime proxetil, cefprozil, cefroxadine, cefsulodin, ceftazidime, cefteram, ceftezole, ceftibuten, ceftiofur, ceftizoxime, ceftriaxone, cefuroxime, cefuzonam, cephacetrile sodium, cephadrine, cephalexin, cephaloglycin, cephaloridine, cephalosporin C, cephalothin, cephapirin sodium, cephradine, chloramphenicol, chlorotetracycline, cinoxacin, ciprofloxacin, claritromycin, clavulanic acid, clinafloxacin, clindamycin, clofazimine, clofoctal, clometocillin, clomocycline, cloxacillin, cloxyquin, cyclacilline, cycloserine, danoflaxcin, dapsone, deoxycycline, deoxydihydrostreptomycin, dicloxacillin, difloxacin, dihydrostreptomycin, dimetridazole, diminazene, dirirtomycin, doripenam, duramycin, eflornithine, enoxacin, enrofloxacin, enviomycin, epicillin, erythromycin, etacillin, ethambutol, ethionamide, famcyclovir, fenbecillin, fleroxacin, flomoxef, floxacillin, flumequine, furonazide, fortimycin, furazolium chloride, gentamycin, glyconiazide, grepafloxacin, guamecycline, halofuginone, hetacillin, homidium, hydroxyl-stilbamidine, ibostamycin, imidocarb, imipenam, ipronidazole, isoniazide, iseganan, iosamycin, inosine, lauroguadine, lenampicillin, levofloxacin, lincomycin, lomefloxacin, loracarbef, lymecyclin, mafenide, mebendazole, meclocyclin, meropenem, metampicillin, metacicline, methacycline, methicillin sodium, metronidazole, 4'-(methylsulfamoyl) sulfanilanilide, mezlocillin, meziocillin, micronomycin, midecamycin $A_1$, minocycline, miocamycin, miokamycin, morfazinamide, moxalactam, mupirocin, myxin, nadifloxacin, nalidixic acid, negamycin, neomycin, netlimycin, nifurfoline, nifurpirinol, nifurprazine, nimorazole, nitroxoline, norfloxacin, novobiocin, ofloxacin, oleandomycin, opiniazide, oxacillin, oxophenarsine, oxolinic acid, oxytetracyclme, panipenam, paromycin, pazufloxacin, pefloxacin, penicillin G potassium salt, penicillin N, penicillin O, penicillin V, penethamate hydroiodide, pentamidine, phenamidine, phenethicillin potassium salt, phenyl aminosalicyclate, pipacycline, pipemidic acid, piperacillin, pirlimycin, piromidic acid, pivampicillin, pivcefalexin, profiromycin, propamidine, propicillin, protionamide, puraltadone, puromycin, pyrazinamide, pyrimethamine, quinacillin, quinacrine, quinapyramine, quintine, ribostamycin, rifabutine, rifamide, rifampin, rifamycin, rifanpin, rifapentine, rifaxymine, ritipenem, rokitamycin, rolitetracycline, rosamycin, rufloxacin, salazosulfadimidine, salinazid, sancycline, sarafloxacin, sedacamycin, secnidazole, sisomycin, sparfloxacin, spectinomycin, spiramycin, spiramycin I, spiramycin II, spiramycin EH, stilbamidine, streptomycin, streptonicizid, sulbactam, sulbenicillin, succisulfone, sulfanilamide, sulfabenzamide, sulfacetamide, sulfachloropyridazine, sulfachrysoidine, sulfacytine, sulfadiazine, sulfadicramide, sulfadimethoxine, sulfadoxine, sulfadrazine, sulfaetidol, sulfafenazol, sulfaguanidine, sulfaguanole, sulfalene, sulfamerazine, sulfameter, sulfamethazine, sulfamethizole, sulfamethomidine, sulfamethoxazole, sulfamethoxypyridazine, sulfamethyltiazol, sulfamethylthiazole, sulfametrole, sulfamidochrysoidine, sulfamoxole, sulfanilamide, 4-sulfanilamido salicylic acid, 4-4'-sulfanilylbenzylamine, p-sulfanilylbenzylamine, 2-p-sulfinylanilinoethanol, sulfanilylurea, sulfoniazide, sulfaperine, sulfaphenazole, sulfaproxyline, sulfapyrazine, sulfapyridine, sulfathiazole, sulfaethidole, sulfathiourea, sulfisomidine, sulfasomizole, sulfasymazine, sulfisoxazole, 4,4'-sulfinyldianiline, $N^4$-sulfanilylsulfanilamide, N-sulfanilyl-3,4-xylamide, sultamicillin, talampicillin, tambutol, taurolidine, teiclplanin, temocillin, tetracycline, tetroxoprim, thiabendazole, thiazolsulfone, tibezonium iodide, ticarcillin, tigemonam, tinidazole, tosufloxacin, trimethoprim, troleandromycin, trospectomycin, trovafloxacin, tubercidine, miokamycin, oleandomycin, troleandromycin, vancomycin, verazide, viomycin, virginiamycin, zalcitabine, acyclovir, amatadine, cidofovir, cytarabine, didanosine, dideoxyadenosine, edoxudine, famciclovir, floxuridine, gancyclovir, idoxuridine, indanavir, kethoxal, lamivudine, MADU, penciclovir, podophyllotoxin, ribavirine, rimantadine, saquinavir, sorivudine, stavudine, trifluridine, valacyclovir, vidarabine, xenazoic acid, zalcitabine, zidovudine, daptomycin, duramycin, nafcillin, and tigecycline.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the invention anticipates and includes within its scope all such isomers and mixtures thereof.

Another embodiment of the invention contemplates the inclusion in the therapeutic composition the organic nitric oxide donor salts of the metabolites of antimicrobials. These metabolites, include but are not limited to, degradation products, hydrolysis products, and the like, of the antimicrobial compound.

The present invention further includes aspects wherein the therapeutic composition further includes one or m ore nitric oxide enhancing compounds that can increase endogenous nitric oxide. Such compounds include for example, nitroxide containing compounds, include, but are not limited to, substituted 2,2,6,6-tetramethyl-1-piperidinyloxy compounds, substituted 2,2,5,5-tetramethyl-3-pyrroline-1-oxyl compounds, substituted 2,2,5,5-tetramethyl-1-pyrrolidinyloxyl compounds, substituted 1,1,3,3-tetramethylisoindolin-2-yloxyl compounds, substituted 2,2,4,4-tetramethyl-1-oxazolidinyl-3-oxyl compounds, substituted 3-imidazolin-1-yloxy, 2,2,5,5-tetramethyl-3-imidazolin-1-yloxyl compounds, OT-551, 4-hydroxy-2,2,6,6-tetramethyl-1-piperidinyloxy (tempol), and the like.

B. Control Release Additives

The therapeutic composition of the invention may also include a controlled release additive. The presence of a controlled release additive in the therapeutic composition substantially reduces the "intitial burst" of biologically active agent released from the therapeutic composition during the initial first 1-2 minutes after delivery to the subject's mucosa. As used herein, the term "substantially reduces" means a decrease of at least 15% of biologically active agent released from the therapeutic composition compared to a composition without the additive. Preferably, the controlled release additive reduces the initial burst of biologically active agent released from the polymeric composition by about 15% to about 70%, more preferably about 30% to about 60%, compared to a therapeutic composition which does not include a controlled release additive.

According to the present disclosure, the controlled release additive is any suitable controlled-release additive, preferably a thermoplastic polymer having poly(lactide-co-glycolide) (PLG) moieties and polyethylene glycol (PEG) moieties. Preferably the controlled release additive is a PLG/PEG block copolymer which includes from about 50 mole % to about 90 mole % lactide monomers and about 50 mole % to about 10 mole % glycolide monomers. More preferably, the PLG/PEG block copolymer includes from about 50 mole % to about 75 mole % lactide monomers and about 50 mole % to about 25 mole % glycolide monomers. Preferably the PEG moiety has a molecular weight of about 1,000 Daltons to about 10,000 Daltons, more preferably about 5000 Daltons. The PEG portion of the block copolymer ranges from about 1 wt % to about 20 wt % of the total weight of the block copolymer. The percentage is dependent on the molecular weight of the block copolymer that is prepared and the molecular weight of the polyethylene glycol that is used. Thus, a block copolymer with a weight average molecular weight of 100,000 Daltons (I.V. approx. 0.8 dL/g) prepared with PEG having a molecular weight of 5,000 Daltons will contain about 5 wt % PEG. If PEG with a molecular weight of 1,000 Daltons is used, the block copolymer will include about 1 wt % of PEG.

The inherent viscosity (abbreviated as "I.V."; units are in deciliters/gram) of the controlled release additive is a measure of its molecular weight. Preferably, the inherent viscosity of the controlled release additive suitable for use with the is compositions of the present disclosure is from about 0.50 dL/g to about 1.0 dL/g (as measured in chloroform), more preferably from about 0.70 dL/g to about 0.90 dL/g.

Suitable polymeric controlled release additives include but are not limited to any PLG/PEG block copolymer with the previously mentioned attributes. Examples of suitable polymeric controlled release additives include, without limitation, 50/50 PLG/PEG-5000 (0.81); 70/30 PLG/PEG-5000 (0.73); and 70/30 PLG/PEG-5000 (0.79).

The controlled release additive, when included in the formulation, may be present in the therapeutic composition in an amount effective to reduce the initial burst of biologically active agent released from the therapeutic composition during the first 2 minutes after delivery to the mucosa. Preferably, the therapeutic composition includes about 1 wt % to about 50 wt %, more preferably about 2 wt % to about 20 wt % of the controlled release additive.

C. Dosage Forms

The therapeutic compositions of the present invention may take the form of solid, semi-solid, lyophilized powder, or liquid dosage forms, such as, for example, tablets (e.g., chewable, slow-dissolving, quick-dissolving), pills, capsules, lozenges, candies, gums, powders, solutions, suspensions, emulsions, aerosols, or the like. Preferably, the dosage form is a chewing gum, quick-dissolving tablet, candy, or lozenge.

While each subject or patient possesses unique factors that may affect the rate and extent of absorption of the therapeutic agents described herein, dosage forms such as chewing gums, candies, quick-dissolving tablets, or lozenges offer advantages over the traditional dosage forms for oral administration. For example, each of these dosage forms avoids hepatic first pass metabolism, degradation within the gastrointestinal tract, and drug loss during absorption. Consequently, the amount is of the active therapeutic agent required per dose is less than that which would be required if formulated, for example, in a pill or tablet for oral administration. Similarly, with each of these dosage forms, the bioavailability of the therapeutic agent is increased, thereby reducing the time to onset of therapeutic activity.

As used herein, the term "dosage form" refers to physically discrete units suitable as unitary dosages for human subjects and other mammals, each unit containing a predetermined quantity of therapeutic agent calculated to produce the desired onset, tolerability, and therapeutic effects, in association with one or more suitable pharmaceutical excipients such as carriers. Methods for preparing such dosage forms are known or will be apparent to those skilled in the art. For example, in some embodiments, a chewing gum dosage form of the present invention can be prepared according to procedures standard in the industry. In other embodiments, a tablet, lozenge, or candy dosage form (e.g., a sucker) of the present invention can be prepared according to the procedures set forth in, for example, Remington's "The Science and Practice of Pharmacy, 20th Ed.," [Lippincott, Williams & Wilkins (2003); and, "Pharmaceutical Dosage Forms, Volume 1: Tablets," 2nd Ed., Marcel Dekker, Inc., New York, N.Y. (1989)]. The dosage form to be administered will, in any event, contain a quantity of the active therapeutic agent in a therapeutically effective amount for relief of the condition being treated when administered in accordance with the teachings of this invention.

As used herein, the term "carrier" refers to a typically inert substance used as a diluent or vehicle for a drug such as a therapeutic agent. The term also encompasses a typically inert substance that imparts cohesive qualities to the composition. Suitable carriers for use in the compositions of the present invention include, without limitation, a solid, semi-solid, or liquid such as a binder or a gum base. Non-limiting examples of binders include mannitol, sorbitol, xylitol, maltodextrin, lactose, dextrose, sucrose, glucose, inositol, powdered sugar, molasses, starch, is cellulose, microcrystalline cellulose, polyvinylpyrrolidone, acacia gum, guar gum, tragacanth gum, alginate, extract of Irish moss, panwar gum, ghatti gum, mucilage of isapol husks, VEEGUM®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. These binders can be pre-processed to improve their flowability and taste by methods known in the art such as freeze drying [see, e.g., "Fundamentals of Freeze-Drying," Pharm. Biotechnol., Vol. 14, pp. 281-360 (2002); "Lyophililization of Unit Dose Pharmaceutical Dosage Forms," Drug. Dev. Ind. Pharm., Vol. 29, pp. 595-602 (2003)]; solid-solution preparation; and lubricant dusting and wet-granulation preparation with a suitable lubricating agent (see, e.g., Remington: The Science and Practice of Pharmacy, supra). For example, MANNOGEM® and SORBOGEM®, sold by SPI Pharma Group (New Castle, Del.), are freeze-dried, processed forms of mannitol and sorbitol, respectively. Typically, when a binder is included in the formulation, the compositions of the present invention comprise from about 15% to about 90% by weight of the binder, and preferably from about 35% to about 80%. However, one skilled in the art will appreciate that the compositions of the present invention can be made without any binders, e.g., to produce a highly friable dosage form.

Non-limiting examples of gum bases include materials selected from among the many water-insoluble and saliva-insoluble gum base materials known in the art. For example, in some instances, the gum base comprises at least one hydrophobic polymer and at least one hydrophilic polymer. Non-limiting examples of suitable hydrophobic and hydrophilic polymers for gum bases include both natural and synthetic polymers such as elastomers, rubbers, and combinations thereof. Examples of suitable natural polymers include, without limitation, substances of plant origin such as chicle, jelutong, gutta percha, crown gum, and combinations thereof. Examples of suitable synthetic polymers include elastomers such as butadiene-styrene copolymers, isobutylene and isoprene copolymers (e.g., "butyl rubber"), polyethylene, is polyisobutylene, polyvinylester (e.g., polyvinyl acetate and polyvinyl acetate phthalate), and combinations thereof. In other instances, the gum base comprises a mixture of butyl rubber (i.e., isobutylene and isoprene copolymer), polyisobutylene, and optionally, polyvinylacetate (e.g., having a molecular weight of approximately 12,000). Typically, the gum base comprises from about 25% to about 75% by weight of these polymers, and preferably from about 30% to about 60%.

The compositions of the present invention can additionally include lubricating agents; wetting agents; emulsifying agents; solubilizing agents; suspending agents; preserving agents such as methyl-, ethyl-, and propyl-hydroxy-benzoates, butylated hydroxytoluene, and butylated hydroxyanisole; sweetening agents; flavoring agents; coloring agents; and disintegrating agents (i.e., dissolving agents) such as crospovidone as well as croscarmellose sodium and other cross-linked cellulose polymers.

Lubricating agents can be used to prevent adhesion of the dosage form to the surface of the dies and punches, and to reduce inter-particle friction. Lubricating agents may also facilitate ejection of the dosage form from the die cavity and improve the rate of granulation flow during processing. Examples of suitable lubricating agents include, without limitation, magnesium stearate, calcium stearate, zinc stearate, stearic acid, simethicone, silicon dioxide, talc, hydrogenated vegetable oil, polyethylene glycol, mineral oil, and combinations thereof. The compositions of the present invention can comprise from about 0% to about 10% by weight of the lubricating agent, and preferably from about 1% to about 5%.

Sweetening agents can be used to improve the palatability of the composition by masking any unpleasant tastes it may have. Examples of suitable sweetening agents include, without limitation, compounds selected from the saccharide family such as the mono-, di-, tri-, poly-, and oligosaccharides; sugars such as sucrose, glucose (corn syrup), dextrose, invert sugar, fructose, maltodextrin, and polydextrose; is saccharin and salts thereof such as sodium and calcium salts; cyclamic acid and salts thereof; dipeptide sweeteners; chlorinated sugar derivatives such as sucralose and dihydrochalcone; sugar alcohols such as sorbitol, sorbitol syrup, mannitol, xylitol, hexa-resorcinol, and the like, and combinations thereof. Hydrogenated starch hydrolysate, and the potassium, calcium, and sodium salts of 3,6-dihydro-6-methyl-1-1,2,3-oxathiazin-4-one-2,2-dioxide may also be used. Of the foregoing, sorbitol, mannitol, and xylitol, either alone or in combination, are preferred sweetening agents. The compositions of the present invention can comprise from about 0% to about 80% by weight of the sweetening agent, preferably from about 5% to about 75%, and more preferably from about 25% to about 50%.

Flavoring agents can also be used to improve the palatability of the composition. Examples of suitable flavoring agents include, without limitation, natural and/or synthetic (i.e., artificial) compounds such as peppermint, spearmint, wintergreen, cinnamon, menthol, cherry, strawberry, watermelon, grape, banana, peach, pineapple, apricot, pear, raspberry, lemon, grapefruit, orange, plum, apple, fruit punch, passion fruit, chocolate (e.g. white, milk, dark), vanilla, caramel, coffee, hazelnut, combinations thereof, and the like. Coloring agents can be used to color code the composition, for example, to indicate the type and dosage of the therapeutic agent therein. Suitable coloring agents include, without limitation, natural and/or artificial compounds such as FD & C coloring agents, natural juice concentrates, pigments such as titanium oxide, silicon dioxide, and zinc oxide, combinations thereof, and the like. The compositions of the present invention can comprise from about 0% to about 10% by weight of the flavoring and/or coloring agent, preferably from about 0.1% to about 5%, and more preferably from about 2% to about 3%.

1. Chewing Gums

When the dosage form is a chewing gum, the compositions of the present invention comprise an active therapeutic agent derived from a gram-positive bacteria or a pharmaceutically acceptable salt thereof, a promoter, a carrier such as a gum is base, a binary or ternary buffer system, and optionally a protecting agent. The chewing gum composition may further comprise lubricating agents, wetting agents, emulsifying agents, suspending agents, preserving agents, sweetening agents, flavoring agents, and coloring agents. Typically, the chewing gum composition comprises from about 0.001% to about 10.0% by weight of the active therapeutic agent (in whatever chosen form, measured as per its free base form), more typically from about 0.01% to about 5.0%, and still more typically from about 0.1% to about 3.0%. One skilled in the art understands that the foregoing percentages will vary depending upon the particular source of gram-positive-based active therapeutic agent utilized, the amount of the active therapeutic agent desired in the final formulation, as well as on the particular release rate of the active therapeutic agent desired. The optional buffer system of the chewing gum composition can provide for a final salivary pH in excess of at least about 8.0, preferably at least about 9.5, and more preferably in the range of from about 9.9 to about 11. The chewing gum composition typically comprises from about 20% to about 95% by weight of the gum base, more typically from about 30% to about 85%, and most typically from about 50% to about 70% of the gum base.

The chewing gum composition may further comprise a protecting agent. The protecting agent coats at least part of the therapeutic agent, typically upon the mixing of the two agents. The protecting agent may be mixed with the active therapeutic agent in a ratio of from about 0.1 to about 100 by weight, preferably in a ratio of from about 1 to about 50, and more preferably in a ratio of about 1 to about 10. Without being bound to any particular theory, the protecting agent reduces the adhesion between the therapeutic agent and the gum base so that the therapeutic agent may be more easily released from the gum base. In this way, the therapeutic agent may be delivered across the mucous membranes of the oral cavity within about 5 to about 20 minutes of chewing, preferably within about 10 minutes of chewing. A variety of different protecting agents may be used. Examples of suitable protecting agents is include, without limitation, calcium stearate, glycerin monostearate, glyceryl behenate, glyceryl palmitostearate, hydrogenated castor oil, hydrogenated vegetable oil type I, light mineral oil, magnesium lauryl sulfate, magnesium stearate, mineral oil, poloxamer, polyethylene gycol, sodium benzoate, sodium chloride, sodium lauryl sulfate, stearic acid, cab-o-sil, talc, zinc stearate, and combinations thereof.

The gum base may additionally include plasticizers such as softeners or emulsifiers. Such plasticizers may, for example, help reduce the viscosity of the gum base to a desirable consistency and improve its overall texture and bite. Plasticizers may also facilitate the release of the therapeutic agent upon mastication. Non-limiting examples of plasticizers include lecithin, mono- and diglycerides, lanolin, stearic acid, sodium stearate, potassium stearate, glycerol triacetate, glycerol monostearate, glycerin, and combinations thereof. The gum base typically comprises from about 0% to about 20% by weight of the plasticizer, and more typically from about 5% to about 15%.

The gum base may further comprise waxes such as beeswax and microcrystalline wax, fats or oils such as soybean and cottonseed oil, and combinations thereof. Typically, the gum base comprises from about 0% to about 25% by weight of these waxes and oils, and more typically comprises from about 15% to about 20%.

In addition, the gum base may further comprise one or more elastomeric solvents such as rosins and resins. Non-limiting examples of such solvents include methyl, glycerol, and pentaerythritol esters of rosins, modified rosins such as hydrogenated, dimerized or polymerized rosins, or combinations thereof (e.g., pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin such as polymers of α-pinene or β-pinene, terpene resins including polyterpene, and is combinations thereof). Typically, the gum base comprises from about 0% to about 75% by weight of the elastomeric solvent, and more typically less than about 10%.

The gum base may further comprise a filler material to enhance the chewability of the final chewing gum composition. Fillers that are substantially non-reactive with other components of the final chewing gum formulation are preferable. Examples of suitable fillers include, without limitation, calcium carbonate, magnesium silicate (i.e., talc), dicalcium phosphate, metallic mineral salts (e.g., alumina, aluminum hydroxide, and aluminum silicates), and combinations thereof. Typically, the gum base comprises from about 0% to about 30% by weight of the filler, and more typically from about 10% to about 20%.

One skilled in the art will appreciate that the gum base need not be prepared from its individual components. For example, the gum base can be purchased with the desired ingredients contained therein, and can be modified to include additional agents. Several manufacturers produce gum bases suitable for use with the described chewing gum compositions. Examples of such gum bases include, without limitation, PHARMGUM™ M, S, or C (SPI Pharma Group; New Castle, Del.). In general, PHARMAGUM™ comprises a mixture of gum base, sweetening agent, plasticizer, and sugar.

In certain instances, the chewing gum composition includes a therapeutic agent centerfill. A centerfill may be particularly suitable when immediate release of the therapeutic agent is preferred. In addition, encapsulating the active therapeutic agent in a centerfill may help to mask any undesirable taste that the therapeutic agent may have. In these instances, the gum base surrounds, at least in part, a centerfill. The centerfill comprises at least one therapeutic agent, and may be a liquid or semi-liquid material. The centerfill material can be a synthetic polymer, a semi-synthetic polymer, low-fat, or fat-free and contain one or more sweetening agents, flavoring agents, coloring agents, and/or scenting agents. Preferably, the centerfill includes a buffer system, including a binary or ternary buffer system as described herein. Methods for preparing a centerfill chewing gum are described, for example, in U.S. Pat. No. 3,806,290, which is hereby incorporated by reference in relevant part.

The chewing gum compositions can have any desired shape, size, and texture. For example, the composition can have the shape of a stick, tab, gumball, and the like. Similarly, the chewing gum can be any desirable color. For example, the chewing gum can be any shade of red, blue, green, orange, yellow, violet, indigo, and mixtures thereof, and can be color coded to indicate the type and dosage of the therapeutic agent therein. The chewing gum can be individually wrapped or grouped together in pieces for packaging by methods well known in the art.

2. Tablets

When the dosage form is a tablet such as a dissolving tablet (i.e., disintegrating tablet) or chewable tablet, the compositions of the present invention comprise a therapeutic agent as described herein derived from one or more gram-positive bacteria, or a pharmaceutically acceptable salt thereof, a promoter, a carrier such as a binder, and a buffer system, including binary or ternary buffer systems. The tablet composition may further comprise lubricating agents, wetting agents, emulsifying agents, suspending agents, preserving agents, sweetening agents, flavoring agents, coloring agents, and disintegrating agents. Typically, the tablet compositions of the present invention comprise from about 0.001% to about 10.0% by weight of the active therapeutic agent (in whatever chosen form, measured as per its free base form), and more typically from about 1.0% to about 5.0%. One skilled in the art understands that the foregoing percentages will vary depending upon the particular source of active therapeutic agent utilized, the amount of the active therapeutic agent desired in the final formulation, as well as on the particular release rate of the active therapeutic agent desired. The buffer system of the tablet composition provides for a final salivary pH in excess of at least about 8.0, preferably at least about 9.5, and more is preferably in the range of from about pH 9.9 to about pH 11.

In certain embodiments, the tablet is a dissolving tablet such as a slow-dissolving or quick-dissolving tablet that is dissolved by a subject's saliva, without the need for chewing. For example, a dissolving tablet placed on the subject's tongue can be used for buccal delivery of the therapeutic agent. Alternatively, a dissolving tablet placed underneath the subject's tongue can be used for sublingual delivery of the therapeutic agent. This type of dosage form may be particularly desirable for pediatric and geriatric patients, since small children and aged individuals often have difficulty chewing certain items. Typically, the dissolving tablet is formulated to dissolve within about 1 to about 15 minutes, preferably within about 2 to about 10 minutes, e.g., within about 2, 3, 4, 5, 6, 7, 8, 9, or 10 minutes, following administration. One skilled in the art will understand that quick-dissolving tablets dissolve faster than slow-dissolving tablets, which are typically dissolved gradually rather than rapidly by a subject's saliva. In a preferred embodiment, the slow-dissolving or quick-dissolving tablet delivers the therapeutic agent across the sublingual mucosa over a period of time greater than about 1 minute.

In certain other embodiments, the tablet is a chewable tablet that is chewed by a subject and formulated to dissolve either rapidly or gradually. For example, a chewable tablet placed on the subject's tongue can be used for buccal delivery of the therapeutic agent. During chewing, the chewable tablet can be moved around within the mouth and can sometimes be parked between the gums and the cheeks or underneath the tongue. As a result, at least a portion of the therapeutic agent contained within a chewable tablet may also be delivered sublingually (i.e., across the sublingual mucosa). Typically, the chewable tablet is formulated to dissolve within about 1 to about 15 minutes, preferably within about 2 to about 10 minutes and not less than 1 minute, e.g., within about 2, 3, 4, 5, 6, 7, 8, 9, or 10 minutes, following administration.

As described above, the dissolving and chewable tablets of the present is invention are typically formulated to dissolve within about 1 to 15 minutes following administration, and preferably not less than about 1 minute. However, while these time frames are amenable to maximum exposure of the therapeutic agent to the oral mucosa (e.g., to the sublingual and/or buccal mucosa), they are not always amenable to user compliance (e.g., users may swallow too frequently and, therefore, hinder maximal transmucosal absorption). Consequently, in certain instances, it may be desirable to strike a balance between patient compliance and maximum exposure time of the therapeutic agent to the oral mucosa. This can be accomplished, for example, by reducing the tablet size (e.g., from about 700-800 mg to about 200-300 mg) without reducing the concentration or amount per unit dose of the buffer system or the therapeutic agent. In addition, subtle changes to the tablet formulation such as, for example, replacing one flavoring agent for another (e.g., chocolate for spearmint) or replacing one binder or sweetening agent for another (e.g., lactose for mannitol or sorbitol) may be used to reduce salivation.

The carrier present in the tablets of the present invention is typically a binder that is useful in keeping the tablet in a semi-solid state, and may be a solid or a liquid, and may for example be a high-melting point fat or waxy material. Materials suitable as binders are discussed in detail above and may be used alone or in combination in the tablet compositions of the present invention. In addition, binders such as mannitol, sorbitol, lactose, sucrose, and inositol can impart properties to the tablet that permit or enhance its disintegration in the mouth.

The tablet composition may further comprise a protecting agent. The protecting agent coats at least part of the therapeutic agent, typically upon the mixing of the two agents. The protecting agent may be mixed with the therapeutic agent in a ratio of from about 0.1 to about 100 by weight, preferably in a ratio of from about 1 to about 50, and more preferably in a ratio of about 1 to about 10. Without being bound to any particular theory, the protecting agent reduces the adhesion between the therapeutic agent and the binder so that the therapeutic agent may be more easily released from the binder. In this way, the therapeutic agent may be delivered across the mucous membranes of the oral cavity within about 5 to about 20 minutes, preferably within about 10 minutes. Materials suitable as protecting agents are discussed in detail above and may be used alone or in combination in the tablet compositions of the present invention.

The tablet composition may also comprise one or more elastomeric solvents such as rosins and resins. Non-limiting examples of such solvents are discussed in detail above and may be used alone or in combination in the tablet compositions of the present invention. In addition, the tablet composition may further comprise waxes such as beeswax and microcrystalline wax, fats or oils such as soybean and cottonseed oil, and combinations thereof. Moreover, the tablet composition may additionally include plasticizers such as softeners or emulsifiers. Such plasticizers may, for example, help reduce the viscosity of the salivary solution of the dissolved tablet to a desirable consistency and improve its overall texture and bite and help facilitate the release of the therapeutic agent. Non-limiting examples of such plasticizers are discussed in detail above and may be used alone or in combination in the tablet compositions of the present invention.

In certain instances, the tablet composition includes a therapeutic agent centerfill. A centerfill may be particularly suitable when immediate release of the therapeutic agent is preferred. In addition, encapsulating the active therapeutic agent in a centerfill may help to mask any undesirable taste that the therapeutic agent may have. In these instances, the binder surrounds, at least in part, a centerfill. The centerfill comprises at least one therapeutic agent in accordance with the present disclosure, and may be a liquid or semi-liquid material. The centerfill material can be low-fat or fat free and contain one or more sweetening agents, flavoring agents, coloring agents, and/or scenting agents. Preferably, the centerfill includes a binary or ternary buffer system as described herein.

In certain other instances, the tablet composition of the present invention is multilayered. In this way, the dissolving or chewable tablet can be designed to provide more than one therapeutic agent, e.g., two or more active therapeutic agents, or one or more active therapeutic agents derived from a first gram-positive bacteria in combination with one or more active therapeutic agents derived from a second gram-positive bacteria. For example, with a bi-layered tablet, the first layer contains a first active therapeutic agent derived from a first gram-positive bacteria, and the second layer contains the same or a different active therapeutic agent derived from the same or a different gram-positive bacteria. Typically, the first layer comprises the dissolving or chewable portion of the tablet, and the second (i.e., subsequent) layer is coated by the first layer. This type of formulation may be particularly suitable when immediate release of the active therapeutic agent, followed by gastrointestinal absorption of a second therapeutic agent, is desirable. Gastrointestinal absorption of the second therapeutic agent may be desirable, for example, in order to mitigate co-morbid symptoms or to sustain the therapeutic benefit of the active therapeutic agent in the dissolving or the chewable portion of the tablet. Alternatively, the second layer is present as a layer lateral to the first layer. The second layer typically comprises at least one therapeutic agent, and can also comprise one or more sweetening agents, flavoring agents, coloring agents, and scenting agents as described above. In some instances, the second layer further includes a binary or ternary buffer system as described herein.

In still other instances, the combination of the active therapeutic agent with or without additional therapeutic agents need not take the form of a multilayered tablet, but instead comprises a single homogenous tablet layer. This type of formulation may also be used in the case where gastrointestinal absorption of at least one therapeutic agent is desirable. In this case, the relative extent of ionization of the two or more therapeutic agents determines how they are to be absorbed. For example, those therapeutic agents that are un-ionized are absorbed through the oral mucosa, while the ionized agents are swallowed for gastrointestinal absorption.

The tablet compositions can have any desired shape, size, and texture. For example, the tablet can have the shape of a stick, tab, pellet, sphere, and the like. Similarly, the tablet can be any desirable color. For example, the tablet can be any shade of red, blue, green, orange, yellow, violet, indigo, and mixtures thereof, and can be color coded to indicate the type and dosage of the therapeutic agent therein. The tablets can be individually wrapped or grouped together in pieces for packaging by methods well known in the art.

3. Lozenges

When the dosage form is a lozenge or candy, the compositions of the present invention comprise the active agent from a gram positive bacteria or a pharmaceutically acceptable salt thereof, an optional promoter, a carrier such as a binder, and a buffer system, including a binary or ternary buffer system; the lozenge or candy composition may further comprise lubricating agents, wetting agents, emulsifying agents, suspending agents, preserving agents, sweetening agents, flavoring agents, coloring agents, and disintegrating agents. A general discussion of lozenges and candies is provided, for example, in "Pharmaceutical Dosage Forms, Volume 1: Tablets" [2nd Ed., Marcel Dekker, Inc., New York, N.Y., pages 75-418 (1989)].

Typically, the lozenge or candy compositions of the present invention comprise from about 0.001% to about 10.0% by weight of the active therapeutic agent (in whatever chosen form, measured as per its free base form), preferably from about 1.0% to about 5.0%, and more preferably from about 2.5% to about 4.5%. One skilled in the art understands that the foregoing percentages will vary depending upon the particular source of the active therapeutic agent utilized, the amount of the active therapeutic agent desired in the final formulation, as well as on the particular release rate of the active therapeutic agent desired. The buffer system for the lozenge or candy composition, when included or necessary, may be a single-compound buffer is system, but is typically a binary or ternary buffer system comprising amorphous magnesium oxide or the like with a carbonate salt and/or a bicarbonate salt. For example, an exemplary ternary buffer system typically comprises from about 4.0% to about 7.0% by weight sodium carbonate; from about 8.0% to about 12.0% by weight desiccant-coated sodium bicarbonate; and from about 20% to about 30% by weight amorphous magnesium oxide. The buffer system provides for a final salivary pH in excess of at least about 8.0 when necessary, preferably at least about 9.5, and more preferably in the range of from about 9.9 to about 11.

In certain embodiments, the lozenge or candy is dissolved by a subject's saliva, without the need for chewing. For example, a lozenge placed on the subject's tongue can be used for buccal delivery of the therapeutic agent. Alternatively, a lozenge placed underneath the subject's tongue can be used for sublingual delivery of the therapeutic agent. This type of dosage form may be particularly desirable for pediatric and geriatric patients, since small children and aged individuals often have difficulty chewing certain items. Typically, the lozenge is formulated to dissolve within about 1 to about 15 minutes, preferably within about 2 to about 10 minutes, and preferably not less than about 1 minute, e.g., within about 2, 3, 4, 5, 6, 7, 8, 9, or 10 minutes, following administration. In a preferred embodiment, the lozenge or candy delivers the therapeutic agent across the sublingual mucosa in a period of time greater than 1 minute.

As described above, the lozenges the present invention are typically formulated to dissolve within about 1 to about 15 minutes following administration, and preferably not less than about 1 minute. However, while these time frames are amenable to maximum exposure of the therapeutic agent to the oral mucosa (e.g., to the sublingual and/or buccal mucosa), they are not always amenable to user compliance (e.g., users may swallow too, frequently and, therefore, hinder maximal transmucosal absorption). Consequently, in certain instances, it may be desirable to strike a balance between patient compliance and maximum exposure time of the therapeutic agent to the oral mucosa. This can be accomplished, for example, by reducing the lozenge size (e.g., from about 700-800 mg to about 200-300 mg) without reducing the concentration or the amount per unit dose of the buffer system or the therapeutic agent. In addition, subtle changes to the lozenge formulation such as, for example, replacing one flavoring agent for another (e.g., chocolate for spearmint) or replacing one binder or sweetening agent for another (e.g., lactose for mannitol or sorbitol) may be used to reduce salivation.

The carrier present in the lozenges of the present invention is typically a binder that is useful in keeping the lozenge in a semi-solid state, and may be a solid or a liquid, and may for example be a high-melting point fat or waxy material. Materials suitable as binders are discussed in detail above and may be used alone or in combination in the lozenge compositions of the present invention. In addition, binders such as mannitol, sorbitol, lactose, sucrose, and inositol can impart properties to the lozenge that permit or enhance its disintegration in the mouth.

The lozenge composition may further comprise a protecting agent. The protecting agent coats at least part of the therapeutic agent, typically upon the mixing of the two agents. The protecting agent may be mixed with the therapeutic agent in a ratio of from about 0.1 to about 100 by weight, preferably in a ratio of from about 1 to about 50, and more preferably in a ratio of about 1 to about 10. Without being bound to any particular theory, the protecting agent reduces the adhesion between the therapeutic agent and the binder so that the therapeutic agent may be more easily released from the binder. In this way, the therapeutic agent may be delivered across the mucous membranes of the oral cavity within about 5 to about 20 minutes, preferably within about 10 minutes. Materials suitable as protecting agents are discussed in detail above and may be used alone or in combination in the lozenge compositions of the present invention.

The lozenge composition may-also comprise one or more elastomeric solvents such as rosins and resins. Non-limiting examples of such solvents are is discussed in detail above and may be used alone or in combination in the tablet compositions of the present invention. In addition, the lozenge composition may further comprise waxes such as beeswax and microcrystalline wax, fats or oils such as soybean and cottonseed oil, and combinations thereof. Moreover, the lozenge composition may additionally include plasticizers such as softeners or emulsifiers. Such plasticizers may, for example, help reduce the viscosity of the salivary solution of the dissolved lozenge to a desirable consistency and improve its overall texture and bite and help facilitate the release of the therapeutic agent. Non-limiting examples of such plasticizers are discussed in detail above and may be used alone or in combination in the lozenge compositions of the present invention.

In certain instances, the lozenge composition includes a therapeutic agent centerfill. A centerfill may be particularly suitable when immediate release of the therapeutic agent is preferred. In addition, encapsulating the therapeutic agent in a centerfill may help to mask any undesirable taste that the therapeutic agent may have. In these instances, the binder surrounds, at least in part, a centerfill. The centerfill comprises at least one therapeutic agent, and may be a liquid or semi-liquid material. The centerfill material can be a synthetic polymer, a semi-synthetic polymer, low-fat, or fat free and contain one or more sweetening agents, flavoring agents, coloring agents, and/or scenting agents. Preferably, the centerfill includes a binary or ternary buffer system as described herein.

In certain other instances, the lozenge composition of the present invention is multilayered. In this way, the lozenge can be designed to provide more than one therapeutic agent, e.g., two or more the therapeutic agents, or one or more the therapeutic agent derived from a first gram-positive bacteria, in combination with one or more therapeutic agents derived from a second gram-positive bacteria. For example, with a bi-layered lozenge, the first layer contains a therapeutic agent derived from *Lactobacillus*, and the second layer contains the same or different therapeutic agent or therapeutic agent derived from a second gram-positive bacteria. Typically, the first layer comprises the dissolving portion of the lozenge, and the second (i.e., subsequent) layer is coated by the first layer. This type of formulation may be particularly suitable when immediate release of the therapeutic agent, followed by gastrointestinal absorption of a second therapeutic agent, is desirable. Gastrointestinal absorption of the second therapeutic agent may be desirable, for example, in order to mitigate co-morbid symptoms or to sustain the therapeutic benefit of the primary therapeutic agent in the dissolving portion of the lozenge. Alternatively, the second layer is present as a layer lateral to the first layer. The second layer typically comprises at least one therapeutic agent, and can also comprise one or more sweetening agents, flavoring agents, coloring agents, and scenting agents as described above. In some instances, the second layer further includes a buffer system as described herein.

In still other instances, the combination of the therapeutic agents with or without non-bacterial therapeutic agents need not take the form of a multilayered lozenge, but instead comprises a single homogenous lozenge layer. This type of formulation may also be used in the case where gastrointestinal absorption of at least one therapeutic agent is desirable. In this case, the relative extent of ionization of the two or more therapeutic agents determines how they are to be absorbed. For example, those therapeutic agents that are un-ionized are absorbed through the oral mucosa, while the ionized agents are swallowed for gastrointestinal absorption.

The lozenge compositions can have any desired shape, size, and texture. For example, the lozenge can have the shape of a stick, tab, pellet, sphere, and the like. Similarly, the lozenge can be any desirable color. For example, the lozenge can be any shade of red, blue, green, orange, yellow, violet, indigo, and mixtures thereof, and can be color coded to indicate the type and dosage of the therapeutic agent therein. The lozenges can be individually wrapped or grouped together in pieces for packaging by methods well known in the art.

In addition to the preferred dosage forms described above, the compositions is of the present invention can also take to form of a solution formulation for delivery of a therapeutic agent as described herein across the oral mucosa. For example, the solution formulation can be administered sublingually by using a two-chamber syringe delivery system, in which the upper chamber contains an unbuffered therapeutic agent solution, the lower chamber contains the dry buffer system components, and a non-permeable membrane separates the upper and lower chambers. Depressing the syringe ruptures the non-permeable membrane and allows mixing of the unbuffered therapeutic agent solution with the dry buffer system components. The resulting buffered therapeutic agent solution is then released from the tip of the syringe. As such, by simply placing the tip of the syringe anywhere underneath a subject's tongue and depressing the syringe, a solution formulation of the present invention can be used to deliver the active therapeutic composition across the subject's sublingual mucosa.

Accordingly, the present invention further provides a composition for delivery of a therapeutic composition across the oral mucosa of a subject for the treatment of a hepatic disease and/or disorder, the composition comprising: (a) a gram-positive bacteria extract, lysate, or a pharmaceutically acceptable salt thereof, preferably from the *Lactobacillus* species of bacteria; (b) an active agent promoter; and, optionally, (c) a buffer system comprising a carbonate salt and/or a bicarbonate salt, wherein the buffer system raises the pH of saliva to a pH greater than about 9.9 irrespective of the starting pH of saliva. Preferably, the composition is a solution that is prepared just prior to administration to the oral mucosa. In certain preferred embodiments, the buffer system comprises sodium bicarbonate and sodium carbonate wherein the ratio of sodium bicarbonate to sodium carbonate ranges from about 1:1 to about 5:1 by weight. In other embodiments, sodium carbonate is used in an amount that is equivalent to, or in excess of sodium bicarbonate. More particularly, the compositions are those that provide peak plasma levels of the active ingredient in less than 15 minutes (e.g, about 1 to about 15 minutes), preferably in about 5 minutes to about 10 minutes.

D. Methods of Administration

The compositions of the present invention are useful in therapeutic applications, e.g., for treating hepatic diseases or disorders, including but not limited to hepatitis A, B and/or C, in subjects in need of such treatment. The methods of the present invention are useful in the treatment of a variety of hepatic disorders, in particular those characterized by an associated link with the alternative pathway in the complement system of the subject. Therefore, according to the present disclosure, a hepatic disorder is any liver disease or disorder in the liver or the surrounding vasculature. For example, the methods and compositions of the present invention are useful in the treatment of a variety of hepatic disorders, including those resulting from infection, iatrogenic disorders, hereditary disorders, autoimmune disorders, cholestatic syndromes, sarcoidosis, organ transplantation, hepatic cancer, and the like.

Exemplary diseases or disorders within the scope of the present disclosure include, but are not limited to, the diseases and disorders detailed in Table 1.

TABLE 1

Exemplary diseases treatable with the compositions of the present disclosure.
Systemic Diseases and Disorders Involving Liver Inflammation A. Hepatitis
  1. Any inflammation of the liver, as for example in acute hepatitis, chronic hepatitis, alcoholic hepatitis and cirrhosis.
  2. Infection
  Any inflammation of the liver resulting from infection, especially viral infection, especially chronic viral hepatitis, for example inflammation associated with:

TABLE 1-continued

Exemplary diseases treatable with the compositions of the present disclosure.
Systemic Diseases and Disorders Involving Liver Inflammation a) Hepatitis A, picorna virus,
b) Hepatitis B, hepadna virus (hepatocellular carcinoma),
c) Hepatitis C, flavivirus,
d) Hepatitis D (Δ), incomplete RNA virus (requires co-infection with hepatitis B),
e) Hepatitis E, single stranded, positive sense RNA genome,
f) Hepatitis F,
g) Hepatitis G (HGBV-C) single stranded RNA virus,
h) Epstein-Barr virus,
i) cytelomegalovirus,
j) adenovirus,
k) other viral infections of the liver
3. Autoimmune
Any inflammation of the liver associated with autoimmune onset of known or unknown etiology, typically associated with significant lymphocyte infiltration in the portal tracts and associated piecemeal necrosis.
4. Iatrogenic
Any drug induced liver inflammation, including for example chronic active hepatitis, cholestasis or granuloma formation.
5. Hereditary
Any inflammation associated with gene-linked trait, for example cirrhotic changes in the liver associated with hepatolenticular degeneration,
a) Wilson's disease
b) α 1-antitrypsin deficiency
c) other inherited metabolic disorders, for example, galactosemia.
B. Cholestatic Syndromes
Any inflammation of the intrahepatic bile ducts, including those resulting in hepatic dysfunction and cirrhosis as for example in primary biliary cirrhosis, primary sclerosing cholangitis and adult idiopathic ductopenia.
C. Transplantations
Any inflammation of the liver or hepatic ducts including that associated with hepatic transplantation, liver injury in graft versus host disease and recipients of renal and other allografts, for example hyperacute allograft rejection, and xenograft rejection.

Particularly preferred disorders within the context of the invention are chronic hepatitis particularly hepatitis resulting from infection, particularly viral infection. Included in this category are the established serological categories of chronic hepatitis, including viral (HBV, HDV, HCV), autoimmune hepatitis (classic lupoid type and subtypes), autoimmune overlap syndromes, drug induced (for example nitrofurantoin, alpha methyldopa, isoniazid) and so-called "cryptogenic" hepatitis In this regard, the skilled artisan will make reference to chapters 8 and 9, and especially Tables 9.2 and 9.3 in "McSween's Pathology of the Liver, 5th Edition (Id.). As the skilled artisan will recognize, some chronic liver diseases not included within the definition of chronic hepatitis may have histological features of chronic hepatitis (for example, piecemeal necrosis). These disorders such as, for example, diseases of intra or extrahepatic bile ducts, are included within the definition herein. Infection with a number of viruses is known to result in serious inflammation of the liver including the hepatitis viruses, hepatitis A (HAV), hepatitis B (HBV), hepatitis C (HCV), hepatitis D (HDV, delta agent) is hepatitis E, hepatitis F and other viruses such as Epstein-Barr virus, cytomegalovirus, adenovirus, paramyovirus, and the like. At least seven types of hepatitis virus (designated A-G) have been identified to date. Of these, one of the most devastating is hepatitis C virus (HCV, also called non-A, non-B). An estimated 3.9 million people in the US are currently infected with HCV, and an estimated 8,000-10,000 deaths each year result from HCV-associated chronic liver disease. Current therapies include γ-interferon, emphasize B and ribivirin, each of which have limited efficacy and serious side effects on the patients. Current therapy also includes transplantation, however, since the infected individual remains infected with the virus, post-transplant immunosuppressed patients exhibit increased viral RNA levels and often rapidly progress to liver disease with the new liver.

Chronic cholestatic syndromes are characterized by progressive inflammatory destruction of intrahepatic bile ducts resulting in hepatic dysfunction, fibrosis and cirrhosis. Examples of this type of disorder include primary biliary cirrhosis, primary sclerosing cholangitis and adult idiopathic ductopenia.

Hereditary disorders treatable by the methods disclosed herein include those inflammatory disorders associated with a gene-linked trait. Examples include but are not limited to Wilson's disease, α1-antitrypsin deficiency and inherited metabolic disorders such as galactosemia and tyrosineanemia.

Other diseases and disorders that can be modulated by the compositions of the present invention include HIV; diabetes; multiple sclerosis (MS); cancer; oxidative stress; brain fog/cognitive dysfunction; peripheral neuropathy; and edema. Preferably, in accordance with one aspect of the disclosure, the disease to be treated or modulated by the natural compositions of the present invention is MS. If multiple sclerosis is to be treated using the natural therapeutic compositions of the present disclosure, the type of multiple sclerosis to be treated is progressive multiple sclerosis, including primary progressive, secondary progressive, or chronic progressive multiple is sclerosis. Alternatively, the type of multiple sclerosis to be treated is relapsing-remitting multiple sclerosis.

Alternatively, in accordance with a further preferred aspect of the disclosure, the disorder to be modulated or treated with the natural compositions of the present disclosure is brain fog/cognitive dysfunction. Cognitive dysfunction (or brain fog) is usually associated with poor mental function, especially regarding concepts, words, memories, and is characterized by confusion, forgetfulness, difficulty in concentration, and maintenance of focus. Sleep patterns are often disturbed and defective REM (dream) sleep may result in serious depressive disorders.

Importantly, the compositions of the present invention provide the rapid delivery of an active therapeutic agent composition of the present disclosure across the oral mucosa, irrespective of the starting pH of saliva. In particular, the delivery of the therapeutic agent across the oral mucosa avoids hepatic first pass metabolism, degradation within the gastrointestinal tract, and therapeutic agent loss during absorption. As a result, the therapeutic agent reaches the systemic circulation in a substantially shorter period of time and at a substantially higher concentration than with traditional oral (e.g., tablet) administration.

The compositions of the present invention have particular utility in the area of human and veterinary therapeutics. Generally, administered dosages will be effective to deliver picomolar to micromolar concentrations of the active composition to the appropriate site.

Administration of the compositions of the present invention may preferably carried out via any of the accepted modes of administration to the mucous membranes of the oral cavity. Examples of suitable sites of administration within the oral mucosa include, without limitation, the mucous membranes of the floor of the mouth (sublingual mucosa), the cheeks (buccal mucosa), the gums (gingival mucosa), the roof of the mouth (palatal mucosa), the lining of the lips, and combinations thereof. These regions is differ from each other with respect to their anatomy, drug permeability, and physiological response to drugs. Preferably, the compositions of the present invention are administered to the sublingual mucosa, buccal mucosa, or a combination thereof.

The oral mucosa, possessing a rich blood supply and suitable drug permeability, is an especially attractive route of administration for systemic delivery of therapeutic agents. Furthermore, delivery of a therapeutic agent across the oral mucosa bypasses hepatic first pass metabolism, avoids enzymatic degradation within the gastrointestinal tract, and provides a more suitable enzymatic flora for drug absorption. As used herein, the term "sublingual delivery" refers to the administration of a therapeutic agent across the mucous membranes lining the floor of the mouth and/or the ventral tongue. The term "buccal delivery" as used herein refers to the administration of a therapeutic agent across the mucous membranes lining the cheeks.

The oral mucosa is composed of an outermost layer of stratified squamous epithelium. Beneath this layer lies a basement membrane, i.e., the lamina propria, followed by the submucosa as the innermost layer. The epithelium of the oral mucosa is similar to the stratified squamous epithelia found in the rest of the body in that it contains a mitotically active basal cell layer, advancing through a number of differentiating intermediate layers to the superficial layers, where cells are shed from the surface of the epithelium. For example, the epithelium of the buccal mucosa is about 40-50 cell layers thick, while that of the sublingual epithelium contains somewhat fewer cell layers. The epithelial cells increase in size and become flatter as they travel from the basal layers to the superficial layers.

The turnover time for buccal mucosal epithelium, estimated at 5-6 days, is representative of the turnover time for sublingual mucosal epithelium as well as other epithelia in the oral mucosa [Harris, et al., J. Pharm. Sci, Vol. 81, pp. 1-10 (1992)]. The thickness of the oral mucosa varies depending on the site in the oral cavity. For is example, the buccal mucosa measures at about 500-800 µm in thickness, while the hard and soft palatal mucosa, the sublingual mucosa, the ventral tongue, and the gingival mucosa measure at about 100-200 µm in thickness. The composition of the epithelium also varies depending on the site in the oral cavity. For example, the mucosae of areas subject to mechanical stress (i.e., the gingivae and hard palate) are keratinized similar to the epidermis. However, the mucosae of the soft palate, the sublingual region, and the buccal region are not keratinized [Harris et al., supra]. The keratinized epithelia contain neutral lipids like ceramides and acylceramides, which have been associated with providing a barrier function. As a result, these epithelia are relatively impermeable to water. In contrast, non-keratinized epithelia, such as sublingual and buccal epithelia, do not contain acylceramides and have only small amounts of ceramide [Wertz, et al., Crit. Rev. Ther. Drug Carr. Sys., Vol. 8, pp. 237-269 (1991); Squier, et al., J. Invest. Dermat., Vol. 96, pp. 123-126 (1991); Squier, et al., in "Oral Mucosal Drug Delivery," Ed. M. J. Rathbone, Marcel Dekker, Inc., New York, N.Y., pp. 1-26 (1996)]. Non-keratinized epithelia also contain small amounts of neutral but polar lipids, e.g., cholesterol sulfate and glucosyl ceramides. As such, these epithelia have been found to be considerably more permeable to water than keratinized epithelia.

In general, the oral mucosa is a somewhat leaky epithelia intermediate between that of the epidermis and intestinal mucosa. For example, the permeability of the buccal mucosa is estimated to be about 4-4000 times greater than that of skin [Galey, et al., J. Invest. Dermat., 67:713-717 (1976)]. The permeability of different regions of the oral mucosa generally decrease in the order of sublingual mucosa greater than buccal mucosa, and buccal mucosa greater than palatal mucosa. This permeability is generally based upon the relative thickness and degree of keratinization of these membranes, with the sublingual mucosa being relatively thin and non-keratinized, the buccal mucosa being thicker and non-keratinized, and the palatal mucosa being intermediate in thickness, but keratinized.

The epithelial cells of the oral mucosa are surrounded by mucus comprising primarily complexes of proteins and carbohydrates that may or may not be attached to certain regions on the cell surface. The mucus may play a role in cell-cell adhesion, as well as acting as a lubricant, allowing cells to move relative to one another [Tabak et al., J. Oral Pathol., 11:1-17 (1982)]. In stratified squamous epithelia found elsewhere in the body, mucus is synthesized by specialized mucus secreting cells such as goblet cells; however, in the oral mucosa, mucus is secreted by the major and minor salivary glands as part of saliva [Tabak, et al., supra; Rathbone, et al., Adv. Drug Del. Rev., 13:1-22 (1994)]. At physiological pH, the mucus network carries a negative charge due to the sialic acid and sulfate residues present on the carbohydrates. At this pH, mucus can form a strongly cohesive gel structure that binds to the epithelial cell surface as a gelatinous layer. Without being bound to any particular theory, the buffer systems of the present invention neutralize the sialic acid residues present on the carbohydrates and prevent them from interacting with the therapeutic agent, thereby further enhancing drug permeation.

Another feature of the environment of the oral cavity is the presence of saliva produced by the salivary glands. Saliva is the protective fluid for all tissues of the oral cavity. Saliva is an aqueous fluid with about 1% organic and inorganic materials. The major determinant of the salivary composition is the flow rate, which in turn depends upon factors such as the time of day, the type of stimulus, and the degree of stimulation. The salivary pH typically ranges from about 5.5 to about 7.0, depending on the flow rate. For example, at high flow rates, the sodium and bicarbonate concentrations increase, leading to an increase in the pH. Because the daily salivary volume is between about 0.5 to about 2 liters, the oral cavity provides an aqueous environment for the hydration and/or dissolution of the oral mucosal dosage forms of the present invention.

The sublingual mucosa is the most highly permeable region of the oral cavity, is and provides rapid absorption and high bioavailability of a drug in a convenient, accessible, and well-accepted route of administration [Harris, et al., supra]. Suitable sublingual dosage forms include, without limitation, tablets (e.g., quick-dissolving, slow-dissolving), lozenges, candy, and soft gelatin capsules filled with liquid drug. Such systems create a very high drug concentration in the sublingual region before they are systemically absorbed across the sublingual mucosa. As a result, the sublingual mucosa is particularly well-suited for producing a rapid onset of action, and sublingual dosage forms can be used to deliver drugs with shorter delivery period requirements and/or less frequent dosing regimens. Although the buccal mucosa is considerably less permeable than the sublingual area, rapid absorption and high bioavailability of a drug can also be observed with buccal administration. Suitable buccal dosage forms include, without limitation, chewing gums, tablets (e.g., quick-dissolving, slow-dissolving), lozenges, candy, and the like. Both the buccal mucosa and the sublingual mucosa are far superior to the gastrointestinal tract for providing increased absorption and bioavailability of a drug.

To increase the permeability of drugs through the oral mucosa, penetration enhancers can be included in the dosage forms of the present invention. The penetration enhancers may be of the type that alters the nature of the oral mucosa to enhance penetration, or of the type that alters the nature of the therapeutic agent to enhance penetration through the oral mucosa. Suitable penetration enhancers include, without limitation, polyoxyethylene 23-lauryl ether, aprotin, azone, benzalkonium chloride, cetylpyridinium chloride, cetyltrimethylammonium bromide, cyclodextrin, dextran sulfate, lauric acid, propylene glycol, lysophosphatidylcholine, menthol, methoxysalicylate, methyloleate, oleic acid; phosphatidylcholine, polyoxyethylene, polysorbate 80, sodium ethylenediaminetetraacetic acid ("EDTA"), sodium deoxycholate, sodium glycocholate, sodium glycodeoxycholate, sodium lauryl suflate, sodium salicylate, sodium taurocholate, sodium taurodeoxycholate, as well as is certain sulfoxides and glycosides, and combinations thereof.

It should be noted that while delivery through the oral mucosa is preferred in accordance with the present disclosure, any method of delivery that delivers the active therapeutic agent to the mucosal wall where it can begin to act therapeutically is envisioned, such alternative mucosal delivery formulations including but not limited to suppositories (both rectal and vaginal), sprays (both oral and nasal), subdermal implants, and controlled release capsules that allow the formulation to move past the stomach region of the patient, e.g., pH controlled release capsules.

E. Mechanisms of Action.

The active therapeutic agent compositions of the present disclosure are believed to be activators of the alternative pathway (AP) in the complement system of innate immunology. While not wishing to be bound by any particular theory, it is believed that the active therapeutic agent compositions of this disclosure work by initiating the cascade of the alternative pathway and driving the formation of C3-convertase. This compound, C3-convertase, subsequently modulates the AP through the C3 amplification loop of complement, forming C5, which is known to exhibit virocidal effects, among others.

Figure 2:
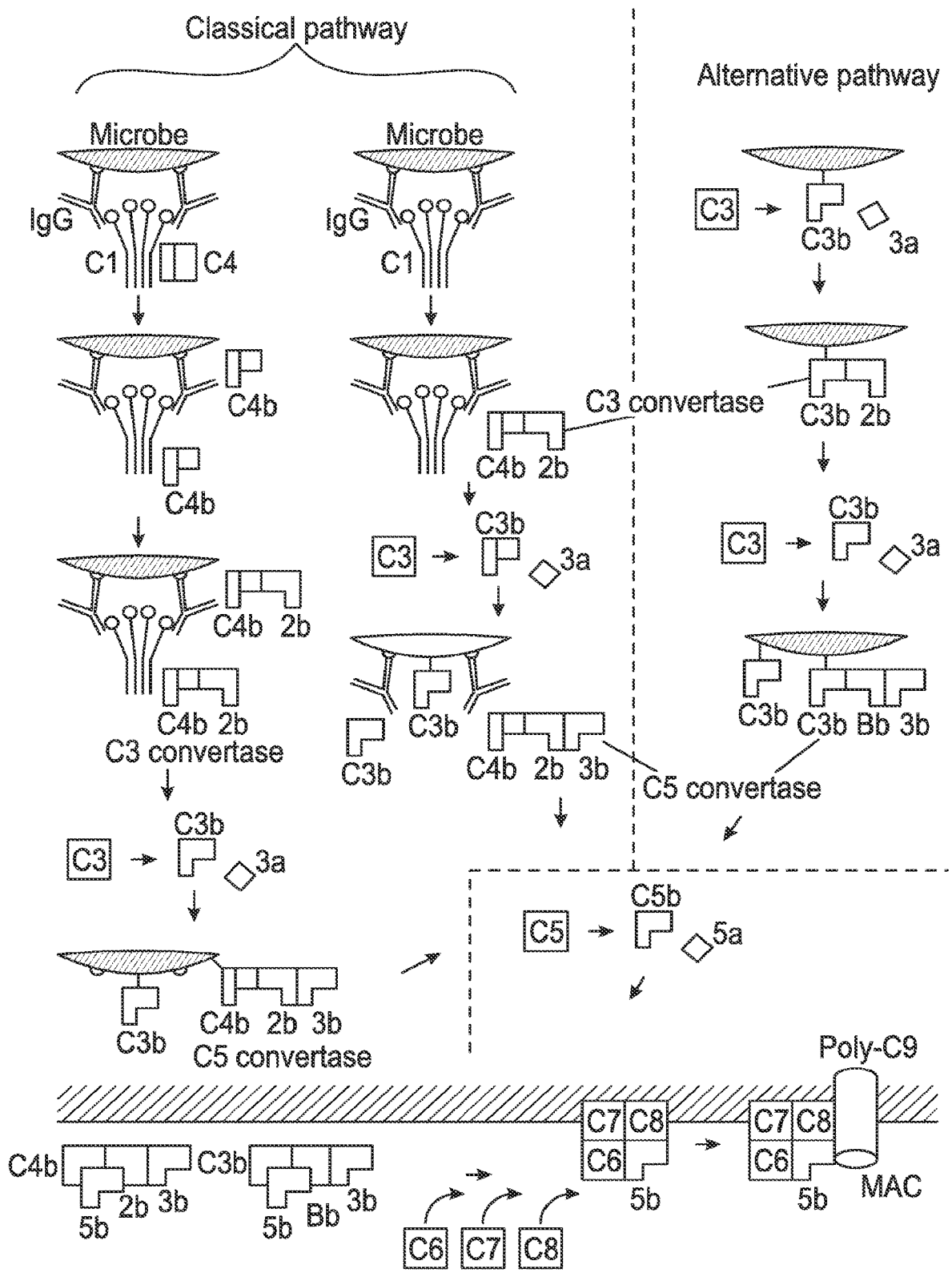
FIG. 2 illustrates a detailed schematic of the classical and alternative complement pathways of FIG. 1.

FIG. 1 illustrates a general diagram of the alternative pathway and complement system. FIG. 2 illustrates the general flow of both the classical and alternative pathways, in accordance with the present disclosure. As shown generally in FIG. 1, the pathway is initiated by the spontaneous hydrolysis of C3, which is abundant in the plasma in the blood. "Tickover" occurs through the spontaneous cleavage of the thioester bond in C3 to form $C3(H_2O)$. This change in shape allows the binding of plasma protein Factor B, which allows Factor D to cleave Factor B into Ba and Bb. Bb remains part of the $C3(H_2O)$ to form $C3(H_2O)Bb$. This complex is also known as a fluid-phase C3-convertase. This convertase, although only produced in small amounts, can cleave multiple C3 proteins into C3a and C3b.

The alternative pathway C3-convertase consists of the activated B and D factors, forming an unstable compound that can become stable after binding properdin, a serum protein. After the creation of C3 convertase, the complement system follows the same path regardless of the means of activation (alternative, classical, or MBL). Binding of another C3b-fragment to the C3-convertase of the alternative pathway creates a C5-convertase analoguous to the MBL or classical pathway. The C5-convertase of the alternative pathway consists of C3bBbC3b also referred to as C3b2Bb (instead of C4b2a3b in the other pathways).

With reference to FIG. 2, both the classical and alternative pathways are shown as general illustrations, with the flow of the pathway presented in more detail than the general schematic of FIG. 1. The classical pathway is triggered by activation of the C1-complex (composed of 1 molecule of C1q, 2 molecules of C1r and 2 molecules of C1s, thus forming $C1qr_2s_2$), which occurs when C1q binds to IgM or IgG complexed with antigens (a single IgM can initiate the pathway, while multiple IgGs are needed), or when C1q binds directly to the surface of the pathogen. Such binding leads to conformational changes in the C1q molecule, which leads to the activation of two C1r (a serine protease) molecules. They then cleave C1s (another serine protease). The $C1r_2s_2$ component now splits C4 and then C2, producing C4a, C4b, C2a, and C2b. C4b and C2b bind to form the classical pathway C3-convertase (C4b2b complex), which promotes cleavage of C3 into C3a and C3b; C3b later joins with C4b2b (the C3 convertase) to make C5 convertase (C4b2b3b complex). The inhibition of C1r and C1s is controlled by C1-inhibitor. C3-convertase can be inhibited by Decay accelerating factor (DAF), which is bound to erythrocyte plasma membranes via a GPI anchor.

The alternative pathway is continuously activated at a low level, analogous to is a car engine at idle, as a result of spontaneous C3 hydrolysis due to the breakdown of the internal thioester bond (C3 is mildly unstable in aqueous environment). The alternative pathway does not rely on pathogen-binding antibodies like the other pathways. C3b that is generated from C3 by a C3 convertase enzyme complex in the fluid phase is rapidly inactivated by factor H and factor I, as is the C3b-like C3 that is the product of spontaneous cleavage of the internal thioester. In contrast, when the internal thioester of C3 reacts with a hydroxyl or amino group of a molecule on the surface of a cell or pathogen, the C3b that is now covalently bound to the surface is protected from factor H-mediated inactivation. The surface-bound C3b may now bind factor B to form C3bB. This complex in the presence of factor D will be cleaved into Ba and Bb. Bb will remain associated with C3b to form C3bBb, which is the alternative pathway C3 convertase. The C3bBb complex is stabilized by binding oligomers of factor P. The stabilized C3 convertase, C3bBbP, then acts enzymatically to cleave much more C3, some of which becomes covalently attached to the same surface as C3b. This newly-bound C3b recruits more B, D and P activity and greatly amplifies the complement activation. When complement is activated on a cell surface, the activation is limited by endogenous complement regulatory proteins, which include CD35, CD46, CD55 and CD59, depending on the cell. Pathogens, in general, don't have complement regulatory proteins (there are many exceptions, which reflect adaptation of microbial pathogens to vertebrate immune defenses). Thus, the alternative complement pathway is able to distinguish self from non-self on the basis of the surface expression of complement regulatory proteins. Host cells don't accumulate cell surface C3b (and the proteolytic fragment of C3b called iC3b) because this is prevented by the complement regulatory proteins, while foreign cells, pathogens and abnormal surfaces may be heavily decorated with C3b and iC3b.

As a result of the effect of the compositions of the present disclosure in regulating (either up-regulating or down-regulating) the alternative pathway in the complement system, the compositions and formulations detailed herein may be used in therapeutic applications to treat a variety of other diseases (in addition to hepatic is diseases and disorders) targeted by Complement, including but not limited to other viral infections, bacterial infections, insulin resistance (type II diabetes), solid tumors, and oxidative stress related diseases, among others, and as set forth above. For example, the natural, non-synthetic gram positive bacterial lystate compositions of the present disclosure can active one or more TLRs or NODs, as discussed in more detail below.

TLRs.

TLRs are conserved molecular receptors that recognize structures from bacteria, fungi, protozoa, and viruses. Activation of TLRs initiates a series of intracellular events resulting in an innate immune response characterized by the production of pro-inflammatory cytokines. TLR signaling originates from the cytoplasmic TIR domain, conserved among all TLRs. The adapter molecule MyD88, containing both a TIR domain and a death domain, associates with the TIR domain of TLRs and IRAK proteins. Phosporylation of IRAK leads to association with TRAF6 and subsequent activation of NF-κB and secretion of pro-inflammatory cytokines. A52R, an immunoregulatory protein from vaccinia virus, has previously been shown to be an intracellular inhibitor of TIR-dependent signaling. When expressed in HEK293 cells, A52R was shown to inhibit NF-κB activation in response to stimulation by a variety of TLRs, including TLR4, TLR5, and the combination of TLR2 and 6, and TLR 2 and 1. In addition, A52R inhibited NF-κB activation in response to Poly (1:0), a synthetic ligand for TLR3. TLR3 has been implicated in an anti-viral innate immune response.

The initiation of an inflammatory response to pathogens is a critical component of the innate immune response and is designed to control infection. However, the sustained production of inflammatory mediators can lead to chronic inflammation, tissue damage and disease development. The signaling cascade initiated by PAMP/TLR interactions and culminating in cell activation has been associated with many disease states, including sepsis, autoimmune diseases, asthma, heart disease and cancer. For example, it is hypothesized that sepsis occurs when is bacteria and their products activate an uncontrolled network of host-derived mediators, such as pro-inflammatory cytokines which can lead to multi-organ failure, cardiovascular collapse and death. An abnormal TLR signaling response could lead to exaggerated cell-activation responses contributing to sepsis. Inflammation is also a key aspect of autoimmunity, and is hypothesized to play a role in tissue destruction in diseases such as multiple sclerosis, rheumatoid arthritis and insulin-dependent diabetes mellitus. Cells of the innate immune system have an essential role in acquired/adaptive immunity. TLR proteins are involved in the maturation and activation of dendritic cells, the antigen-presenting cell type considered most relevant to development of acquired immunity. Allergic asthma is an example of a chronic inflammatory disease with an adaptive immune response, and the TLR signaling pathway is hypothesized to play an important role in the induction phase of an allergic phenotype. Bacterial and viral infections, causing increased inflammatory cell activation, are the main cause of exacerbations in diseases such as asthma and COPD (chronic obstructive pulmonary disease). Understanding and manipulating the TLR cell activation pathway has the potential to provide therapeutic benefit for a variety of diseases with an inflammatory etiology. Treatments for inflammation have included the use of aspirin and glucocorticoids to block NF-κB activation and the targeting of specific inflammatory mediators such as TNF-α. Recent studies report blocking the interaction of TLRs and their ligands, or suppressing TLR expression may provide new approaches for controlling inflammation. The identification of proteins involved in TIR signaling, and their molecular characterization, have lead to development of agents to inhibit specific points within the TIR signaling cascade. Inhibition of multiple TLR-dependent responses, by targeting a common signaling component, may prove to be a more effective approach to controlling an inflammatory response. Thus, in accordance with further aspects of the present disclosure, the compositions of the present invention may be used to treat an inflammatory or other disorder associated with the complement system that is a TLR-associated disorder is (e.g., TLR-induced inflammation), the method comprising the administration of a therapeutically effective amount of a composition as described herein, wherein the TLR affected is one or more of TLR 2, TLR 3, TLR 4, TLR 5, TLR 7, TLR 8 and TLR 9.

In accordance with further embodiments of the present disclosure, the compositions of the present invention may modulate or otherwise affect the Nod2 protein and/or nucleic acids encoding the Nod2 protein. The Nod2 protein has been found to have structural homology to the Nod1 protein. Apaf-1 and Nod1 (also called CARD4) are members of a family of intracellular proteins that are composed of an $NH_2$-terminal caspase-recruitment domain (CARD), a centrally located nucleotide-binding domain (NBD) and a COOH-terminal regulatory domain [Bertin, et al., J. Biol. Chem. 274: 12955-12958 (1999); Inohara, et al., J. Biol. Chem. 274: 14560-14568 (1999)]. While Apaf-1 possesses WD40 repeats, Nod1 contains leucine-rich repeats (LRRs) in its C-terminus. The structural and functional similarities between Apaf-1 and Nod1 suggest that these proteins share a common molecular mechanism for activation and effector function. In the case of Apaf-1, the WD-40 repeats act as a recognition domain for mitochondrial damage through binding to cytochrome c, allowing Apaf-1 to oligomerize and interact with procaspase-9 through a CARD-CARD homophilic interaction [Zou, et al., J. Bio. Chem. 274: 11549-11556 (1999)]. Apaf-1 oligomerization is mediated by the NBD and is thought to induce the proximity and proteolytic activation of procaspase-9 molecules in the apoptosome complex [Hu, et al., J. Bio. Chem. 273: 33489 34494 (1998)].

Nod2 is a LRR-containing protein with structural and functional similarity to Nod1. Studies have indicated that Nod2 activates NF-kB, but unlike Nod1, Nod2 is primarily expressed in monocytes. The present invention is not limited to any particular mechanism of action. Indeed, an understanding of the mechanism of action is not necessary to practice the present invention. Nevertheless, Nod2 is a member of the Nod1/Apaf-I family that activates NF-κB through interactions with its $NH_2$-terminal CARDS, as these domains are apparently necessary and sufficient for NF-κB is activation. Additionally, Nod2 is associated with RICK via a homophilic CARD-CARD interaction.

In accordance with other aspects of the present disclosure, the compositions described herein may be used therapeutically to stimulate CdK5 in a subject upon administration of the composition. Cdk5, a member of the cyclin-dependent kinase (cdk) family, is predominately active in neurons, where its activity is tightly regulated by the binding of its neuronal activators p35 and p39. Cdk5 has been implicated in regulating the proper neuronal function; further, a deregulation of Cdk5 has been found associated with Alzheimer's disease and amyotrophic lateral sclerosis. In accordance with the present disclosure, it is expected that the natural, non-synthetic compositions of the invention will exhibit positive, therapeutic effects on Cdk5 activity and on the expression of Cdk5 and p35 proteins in subjects. For example, it is believed that the compositions of the present disclosure, when administered to a subject in need thereof, stimulate Cdk5 activity and induce an upregulation of its regulatory and catalytic subunit expression in vital cells.

The following examples are included to demonstrate preferred embodiments of the inventions. It should be appreciated by those of skill in the art that the techniques disclosed in the examples which follow represent techniques discovered by the inventors to function well in the practice of the inventions, and thus can be considered to constitute preferred modes for its practice. However, those of skill in the art should, in light of the present disclosure, appreciate that many changes can be made in the specific embodiments which are disclosed and still obtain a like or similar result without departing from the scope of the inventions.

EXAMPLES

Example 1: Active Ingredient Composition Preparation

In order to prepare an exemplary formulation as described herein suitable for therapeutic testing and further cell line testing, such as in screening tests and subject testing.

Active Ingredient.

The active ingredient is a gram positive bacteria, such as described herein above. In example, *Lactobacillus delbrueckii*, ssp. *Bulgaricus* was used, employing a fermentation and cell isolation process as carried out by Kerry Ingredients & Flavours (Beloit, Wis.) and as described generally below.

Fermentation.

Cells of a gram positive bacteria, *Lactobacillus delbrueckii* subsp. *Bulgaricus*, was fermented in 500 L of an appropriate media for approximately 120 hours.

Cell Isolation.

The 500 L of broth was centrifuged and the resultant cell mass was washed three times with DI water. This produced approximately 60 kg of wet cell mass.

Lysing and Purification.

The wet cell mass was reconstituted and the pH is adjusted to 6.8-7.0. Lysozyme chloride (extracted from hen egg whites) was added to make a solution with a concentration of 500 ppm of lysozyme chloride. The slurry was agitated and the temperature is maintained at 40-50° C. for 24 hours. After lysing, the active components were in the liquid phase. This liquid material containing the water soluble active components was recovered through centrifugation to remove the solid material, and then washed three times with DI water. The resultant mixture was frozen in pellets and the remaining solid material in the centrifuge was discarded.

Formulation.

The frozen pellets were freeze dried to form a dry powder and milled, as necessary. This material was blended with a promoter, such as N-acetyl D-glucosamine HCl (NAG), to form a mixture of lysed *Lactobacillus delbrueckii* subsp. *Bulgaricus* and NAG. Optionally, other formulation excipients to generate a solid form pill or powder were added, as appropriate. This product was then used in the following screening tests.

Example 2: TLR Screening

TLR stimulation was tested by assessing NF-κB activation in HEK293 cells expressing a given TLR or NLR. The activities of the samples were tested on seven different human TLRs: TLR2, 3, 4, 5, 7, 8 and 9 (Invivogen, San Diego, Calif.), and on two different human NLRs (NOD1 and NOD2). Each ligand was tested at a final concentration of $\frac{1}{100}$ of the stock solution on the TLR or NLR cells, and compared to control ligands, as described below. This step was performed in triplicate.

The control ligands, control cell lines, and sample product used in the examples were as shown in Table 2.

TABLE 2

Control ligands and control cell line information used in ligand screening tests.

| | |
|---|---|
| Control Ligands | TLR2: HKLM (heat-killed *Listeria monocytogenes*) at $10^8$ cells/mL. |
| | TLR3: Poly(I:C) at 1 µg/mL |
| | TLR4: *E. coli* K12 LPS at 100 ng/mL |
| | TLR5: |
| | TLR7: CL097 at 1 µg/mL |
| | TLR8: CL075 at 1 µg/mL |
| | TLR9: CpG ODN 2006 at 100 ng/mL |
| | NOD1: C12iEDAP at 10 µg/mL |
| | NOD2: L18-MDP at 100 ng/mL |
| Control Cell Lines | HEK293/Null1: TNFα at 1 µg/mL (control for human TLR 2, 3, 5, 8, 9 and NOD 1) |
| | HEK293/Null1-k: TNFα at 1 µg/mL (control for human TLR7) |
| | HEK293/Null2: TNFα at 1 µg/mL (control for human TLR4 and NOD2) |
| Sample | Lysate of *Lactobacillus delbrueckii* subsp. *Bulgaricus* ($\frac{1}{10}$ dilution prepared in sterile, endotoxin-free water) |

General Procedure.

TLR stimulation in the screening is tested by assessing NF-κB activation in the HEK293 cells expressing a given TLR. The secreted alkaline phosphatase reporter is under the control of a promoter inducible by the transcription factor NF-κB. TLR stimulation in the screening was tested by assessing NF-κB activation in the HEK293 cells expressing a given TLR or NLR. This reporter gene allows the monitoring of signaling through the TLR/NLR, based on the activation of NF-κB. In a 96-well plate (200 µL total volume) containing the appropriate cells (50,000-75,000 cells/well), 20 µL of the Sample (lysate product) or the positive control ligands to the wells. The media added to the wells is designed for the detection of NF-κB induced SEAP (secreted alkaline phosphatase) expression. After a 16-20 hr incubation, the OD (optical density) at 650 nm was read on an Molecular Devices Spectra Max 340PC absorbance detector and recorded.

Figure 3:
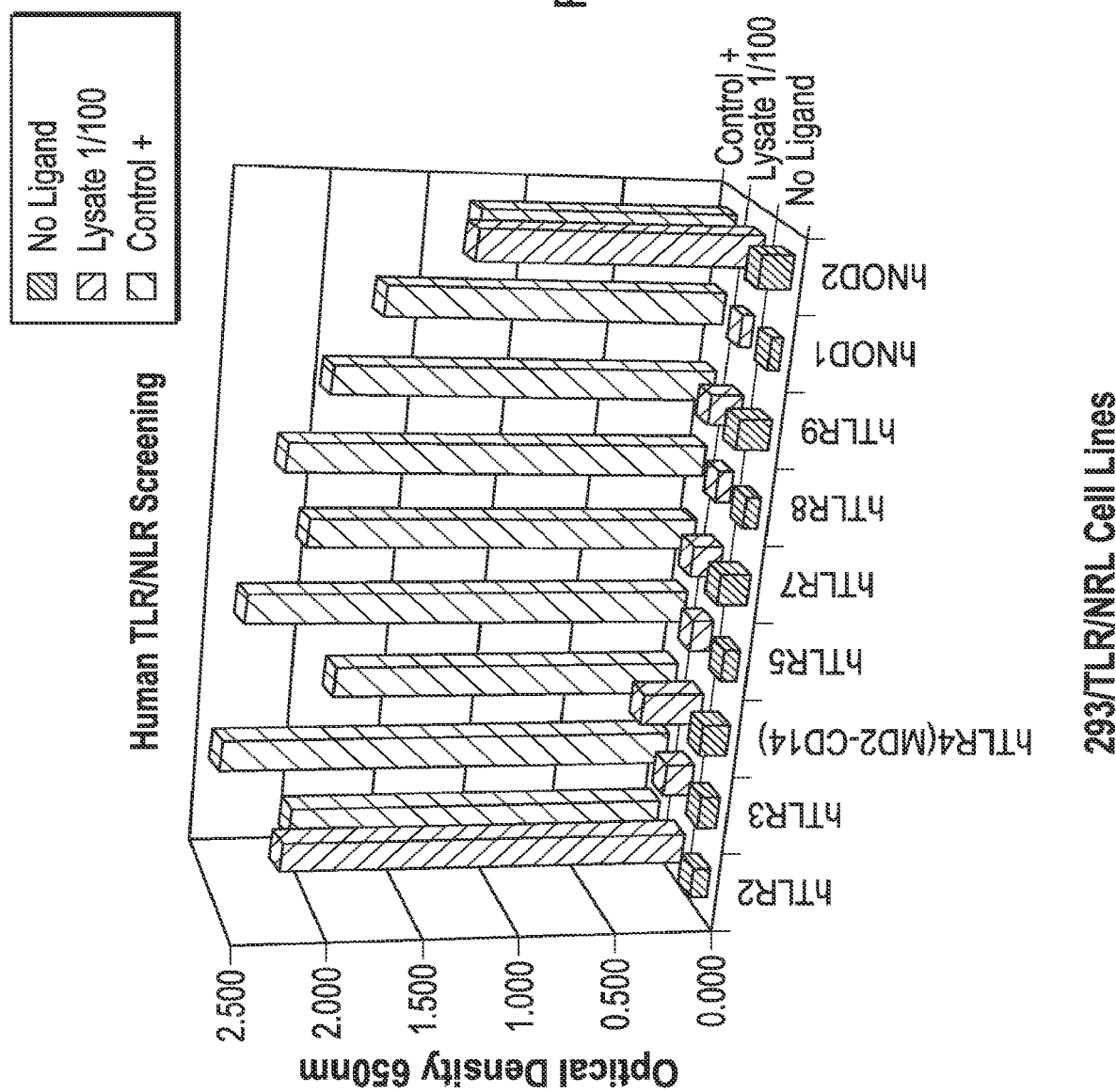
FIG. 3 illustrates a graph of exemplary stimulatory effects of a composition of the present invention on select TLR/NLR cell lines; the values in the graph correspond to an average of screenings 1-3.
Figure 4:
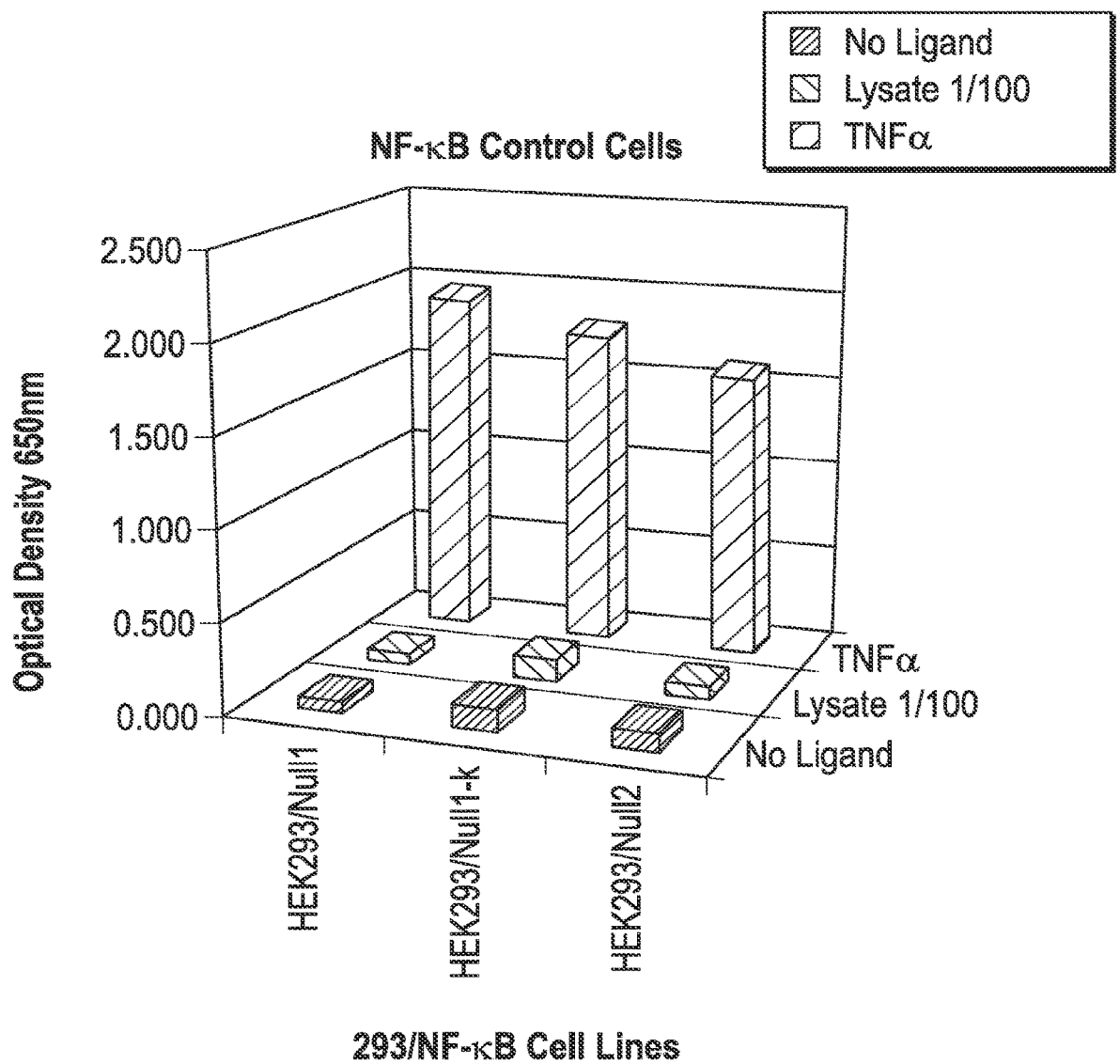
FIG. 4 illustrates a graph of stimulatory effects of control and sample compositions of the present invention against NF-κB control cells; the values in the graph correspond to an average of screenings 1-3.

The screening results of these experiments are shown graphically in FIG. 3, and in the screening data result tables shown in FIG. 5. Control cell line comparisons are shown graphically in FIG. 4, and in the data shown in the summary tables of FIG. 6. In view of these results, it is clear that the lysate sample tested activates human TLR2, 4 and NOD2 at a $\frac{1}{100}$ concentration.

Other and further embodiments utilizing one or more aspects of the inventions described above can be devised without departing from the spirit of Applicant's invention. For example, the two or more active ingredients from two separate gram positive bacteria can be used in formulating the active composition for use in therapeutic application. Further, the various methods and embodiments of the methods of oral administration can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

The invention claimed is:

1. A liquid formulation comprising:
   (a) a lysate and/or cell wall extract from a Gram-positive bacterium comprising a toll-like receptor (TLR) ligand that activates at least one or more TLRs or Nod-like receptors (NLRs), or a pharmaceutically acceptable salt thereof; and
   (b) a buffer;
   wherein the liquid formulation comprises a promoter;
   wherein the promoter is selected from the group consisting of amino acids, amino sugars, and sugars; and
   wherein the promoter is selected from the group consisting of poly-L-lysine, glucosamine, poly-L-arginine, galactosamine, N-acetylmannosamine (NAM; N-Ac-Man), N-acetylglucosamine (NAG; N-Ac-Glc), N,N'-diacetylglucosamine (NAG-NAG; N,N'-diacetylchitobiose), N,N',N'',N'''-tetraacetylglucosamine (NAG-NAG-NAG-NAG; N,N',N'',N'''-tetraacetylchitotetraose), and mixtures thereof.

2. A liquid formulation comprising:
   (a) a lysate and/or cell wall extract from a Gram-positive bacterium comprising a toll-like receptor (TLR) ligand that activates at least one or more TLRs or Nod-like receptors (NLRs), or a pharmaceutically acceptable salt thereof; and
   (b) a buffer;
   wherein the liquid formulation further comprises a non-steroidal anti-inflammatory drug (NSAID).

3. A liquid formulation comprising:
   (a) a lysate and/or cell wall extract from a Gram-positive bacterium comprising a toll-like receptor (TLR) ligand that activates at least one or more TLRs or Nod-like receptors (NLRs), or a pharmaceutically acceptable salt thereof; and
   (b) a buffer;
   wherein the liquid formulation further comprises a chemotherapeutic agent.

4. A liquid formulation comprising:
   (a) a lysate and/or cell wall extract from a Gram-positive bacterium comprising a toll-like receptor (TLR) ligand that activates at least one or more TLRs or Nod-like receptors (NLRs), or a pharmaceutically acceptable salt thereof; and
   (b) a buffer;
   wherein the liquid formulation further comprises a surfactant.

* * * * *